(12) United States Patent
Rolando et al.

(10) Patent No.: US 8,685,084 B2
(45) Date of Patent: Apr. 1, 2014

(54) PROSTHETIC VASCULAR CONDUIT AND ASSEMBLY METHOD

(71) Applicant: Sorin Group Italia S.r.l., Milan (IT)

(72) Inventors: Giovanni Rolando, Chivasso (IT);
Paolo Gaschino, Castagneto Po (IT);
Monica Achiluzzi, Chivasso (IT); Felice Giuseppe Carlino, Borgomasino (IT)

(73) Assignee: Sorin Group Italia S.r.l., Milan (IT)

( * ) Notice: Subject to any disclaimer, the term of this patent is extended or adjusted under 35 U.S.C. 154(b) by 0 days.

(21) Appl. No.: 13/729,636

(22) Filed: Dec. 28, 2012

(65) Prior Publication Data

US 2013/0172991 A1 Jul. 4, 2013

(30) Foreign Application Priority Data

Dec. 29, 2011 (EP) .................................... 11425310

(51) Int. Cl.
*A61F 2/24* (2006.01)
(52) U.S. Cl.
USPC ......................................................... 623/2.11
(58) Field of Classification Search
USPC ............. 623/2.1, 2.11, 1.24–1.26, 1.11–1.12, 623/1.23; 606/108, 149, 153; 600/36
See application file for complete search history.

(56) References Cited

U.S. PATENT DOCUMENTS

| | | |
|---|---|---|
| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,608,097 A | 9/1971 | Bellhouse et al. |
| 3,628,535 A | 12/1971 | Ostrowsky et al. |
| 3,642,004 A | 2/1972 | Osthagen et al. |
| 3,657,744 A | 4/1972 | Ersek |

(Continued)

FOREIGN PATENT DOCUMENTS

| | | |
|---|---|---|
| CN | 101011298 A | 8/2007 |
| DE | 3640745 A1 | 6/1987 |

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Darwin Erezo
*Assistant Examiner* — Amy Shipley
(74) *Attorney, Agent, or Firm* — Faegre Baker Daniels LLP

(57) ABSTRACT

A kit for implanting a prosthetic vascular conduit includes a prosthetic vascular conduit for coupling to a prosthetic valve having an annular portion. The conduit includes a terminal collar member for receiving the valve. The kit further includes a holder including a shaft and a hub including a receiving portion configured for housing a prosthetic valve. The conduit is fitted on the holder so that at least a portion of the conduit wraps over the receiving portion of the hub. A sleeve member fitted onto the conduit in a position corresponding to the receiving portion of the hub, and a portion of the collar member is wrapped or folded over the sleeve member. The sleeve member is slidable away from the hub to unwrap the collar member such that it is disposed around the annular portion of a prosthetic valve.

17 Claims, 11 Drawing Sheets

(56) References Cited

U.S. PATENT DOCUMENTS

| | | | |
|---|---|---|---|
| 3,671,979 A | 6/1972 | Moulopoulos | |
| 3,744,060 A | 7/1973 | Bellhouse et al. | |
| 3,755,823 A | 9/1973 | Hancock | |
| 3,795,246 A | 3/1974 | Sturgeon | |
| 3,839,741 A | 10/1974 | Haller | |
| 3,868,956 A | 3/1975 | Alfidi et al. | |
| 3,874,388 A | 4/1975 | King et al. | |
| 3,997,923 A | 12/1976 | Possis | |
| 4,035,849 A | 7/1977 | Angell et al. | |
| 4,056,854 A | 11/1977 | Boretos et al. | |
| 4,086,665 A | 5/1978 | Poirier | |
| 4,106,129 A | 8/1978 | Carpentier et al. | |
| 4,222,126 A | 9/1980 | Boretos et al. | |
| 4,233,690 A | 11/1980 | Akins | |
| 4,265,694 A | 5/1981 | Boretos et al. | |
| 4,291,420 A | 9/1981 | Reul | |
| 4,297,749 A | 11/1981 | Davis et al. | |
| 4,339,831 A | 7/1982 | Johnson | |
| 4,343,048 A | 8/1982 | Ross et al. | |
| 4,345,340 A | 8/1982 | Rosen | |
| 4,425,908 A | 1/1984 | Simon | |
| 4,451,936 A | 6/1984 | Carpentier et al. | |
| 4,470,157 A | 9/1984 | Love | |
| 4,477,930 A | 10/1984 | Totten et al. | |
| 4,501,030 A | 2/1985 | Lane | |
| 4,506,394 A | 3/1985 | Bedard | |
| 4,574,803 A | 3/1986 | Storz | |
| 4,580,568 A | 4/1986 | Gianturco | |
| 4,592,340 A | 6/1986 | Boyles | |
| 4,610,688 A | 9/1986 | Silvestrini et al. | |
| 4,612,011 A | 9/1986 | Kautzky | |
| 4,624,822 A | 11/1986 | Arru et al. | |
| 4,647,283 A | 3/1987 | Carpentier et al. | |
| 4,648,881 A | 3/1987 | Carpentier et al. | |
| 4,662,885 A | 5/1987 | DiPisa, Jr. | |
| 4,665,906 A | 5/1987 | Jervis | |
| 4,681,908 A | 7/1987 | Broderick et al. | |
| 4,692,164 A | 9/1987 | Dzemeshkevich et al. | |
| 4,710,192 A | 12/1987 | Liotta et al. | |
| 4,758,151 A | 7/1988 | Arru et al. | |
| 4,777,951 A | 10/1988 | Cribier et al. | |
| 4,787,899 A | 11/1988 | Lazarus | |
| 4,796,629 A | 1/1989 | Grayzel | |
| 4,797,901 A | 1/1989 | Goerne et al. | |
| 4,819,751 A | 4/1989 | Shimada et al. | |
| 4,834,755 A | 5/1989 | Silvestrini et al. | |
| 4,856,516 A | 8/1989 | Hillstead | |
| 4,872,874 A | 10/1989 | Taheri | |
| 4,878,495 A | 11/1989 | Grayzel | |
| 4,878,906 A | 11/1989 | Lindemann et al. | |
| 4,883,458 A | 11/1989 | Shiber | |
| 4,909,252 A | 3/1990 | Goldberger | |
| 4,917,102 A | 4/1990 | Miller et al. | |
| 4,922,905 A | 5/1990 | Strecker | |
| 4,966,604 A | 10/1990 | Reiss | |
| 4,979,939 A | 12/1990 | Shiber | |
| 4,986,830 A | 1/1991 | Owens et al. | |
| 4,994,077 A | 2/1991 | Dobben | |
| 5,002,559 A | 3/1991 | Tower | |
| 5,007,896 A | 4/1991 | Shiber | |
| 5,026,366 A | 6/1991 | Leckrone | |
| 5,032,128 A | 7/1991 | Alonso | |
| 5,037,434 A | 8/1991 | Lane | |
| 5,047,041 A | 9/1991 | Samuels | |
| 5,059,177 A | 10/1991 | Towne et al. | |
| 5,061,273 A | 10/1991 | Yock | |
| 5,084,151 A | 1/1992 | Vallana et al. | |
| 5,085,635 A | 2/1992 | Cragg | |
| 5,089,015 A | 2/1992 | Ross | |
| 5,123,919 A * | 6/1992 | Sauter et al. | 623/1.26 |
| 5,133,845 A | 7/1992 | Vallana et al. | |
| 5,139,515 A | 8/1992 | Robicsek | |
| 5,152,771 A | 10/1992 | Sabbaghian et al. | |
| 5,161,547 A | 11/1992 | Tower | |
| 5,163,953 A | 11/1992 | Vince | |
| 5,163,954 A | 11/1992 | Curcio et al. | |
| 5,167,628 A | 12/1992 | Boyles | |
| 5,217,483 A | 6/1993 | Tower | |
| 5,232,445 A | 8/1993 | Bonzel | |
| 5,272,909 A | 12/1993 | Nguyen et al. | |
| 4,733,665 B1 | 1/1994 | Palmaz | |
| 5,295,958 A | 3/1994 | Shturman | |
| 5,314,468 A | 5/1994 | Ramos Martinez | |
| 5,327,774 A | 7/1994 | Nguyen et al. | |
| 5,332,402 A | 7/1994 | Teitelbaum | |
| 5,350,398 A | 9/1994 | Pavcnik et al. | |
| 5,370,684 A | 12/1994 | Vallana et al. | |
| 5,370,685 A | 12/1994 | Stevens | |
| 5,387,247 A | 2/1995 | Vallana et al. | |
| 5,389,106 A | 2/1995 | Tower | |
| 5,397,351 A | 3/1995 | Pavcnik et al. | |
| 5,411,552 A | 5/1995 | Andersen et al. | |
| 5,415,633 A | 5/1995 | Lazarus et al. | |
| 5,423,886 A | 6/1995 | Arru et al. | |
| 5,431,676 A | 7/1995 | Dubrul et al. | |
| 5,443,446 A | 8/1995 | Shturman | |
| 5,449,384 A | 9/1995 | Johnson | |
| 5,480,424 A | 1/1996 | Cox | |
| 5,489,294 A | 2/1996 | McVenes et al. | |
| 5,489,297 A | 2/1996 | Duran | |
| 5,496,346 A | 3/1996 | Horzewski et al. | |
| 5,507,767 A | 4/1996 | Maeda et al. | |
| 4,954,126 B1 | 5/1996 | Wallsten | |
| 5,545,209 A | 8/1996 | Roberts et al. | |
| 5,545,211 A | 8/1996 | An et al. | |
| 5,545,214 A | 8/1996 | Stevens | |
| 5,545,215 A | 8/1996 | Duran | |
| 4,655,771 B1 | 9/1996 | Wallsten | |
| 5,554,185 A | 9/1996 | Block et al. | |
| 5,575,818 A | 11/1996 | Pinchuk | |
| 5,580,922 A | 12/1996 | Park et al. | |
| 5,591,195 A | 1/1997 | Taheri et al. | |
| 5,609,626 A * | 3/1997 | Quijano et al. | 623/1.24 |
| 5,645,559 A | 7/1997 | Hachtman et al. | |
| 5,665,115 A | 9/1997 | Cragg | |
| 5,667,523 A | 9/1997 | Bynon et al. | |
| 5,674,277 A | 10/1997 | Freitag | |
| 5,695,498 A | 12/1997 | Tower | |
| 5,702,368 A | 12/1997 | Stevens et al. | |
| 5,712,953 A | 1/1998 | Langs | |
| 5,713,953 A | 2/1998 | Vallana et al. | |
| 5,716,417 A | 2/1998 | Girard et al. | |
| 5,746,709 A | 5/1998 | Rom et al. | |
| 5,749,890 A | 5/1998 | Shaknovich | |
| 5,766,151 A | 6/1998 | Valley et al. | |
| 5,782,809 A | 7/1998 | Umeno et al. | |
| 5,800,456 A | 9/1998 | Maeda et al. | |
| 5,800,508 A | 9/1998 | Goicoechea et al. | |
| 5,817,126 A | 10/1998 | Imran | |
| 5,824,037 A | 10/1998 | Fogarty et al. | |
| 5,824,041 A | 10/1998 | Lenker et al. | |
| 5,824,043 A | 10/1998 | Cottone, Jr. | |
| 5,824,053 A | 10/1998 | Khosravi et al. | |
| 5,824,056 A | 10/1998 | Rosenberg | |
| 5,824,061 A | 10/1998 | Quijano et al. | |
| 5,824,064 A | 10/1998 | Taheri | |
| 5,840,081 A | 11/1998 | Andersen et al. | |
| 5,843,158 A | 12/1998 | Lenker et al. | |
| 5,843,244 A | 12/1998 | Pelton et al. | |
| 5,851,232 A | 12/1998 | Lois | |
| 5,855,597 A | 1/1999 | Jayaraman | |
| 5,855,601 A | 1/1999 | Bessler et al. | |
| 5,860,996 A | 1/1999 | Urban et al. | |
| 5,861,028 A | 1/1999 | Angell | |
| 5,868,783 A | 2/1999 | Tower | |
| 5,876,436 A | 3/1999 | Vanney et al. | |
| 5,876,448 A | 3/1999 | Thompson et al. | |
| 5,888,201 A | 3/1999 | Stinson et al. | |
| 5,891,191 A | 4/1999 | Stinson | |
| 5,891,195 A * | 4/1999 | Klostermeyer et al. | 623/1.26 |
| 5,906,619 A | 5/1999 | Olson et al. | |
| 5,907,893 A | 6/1999 | Zadno Azizi et al. | |
| 5,913,842 A | 6/1999 | Boyd et al. | |
| 5,925,063 A | 7/1999 | Khosravi | |

(56) References Cited

U.S. PATENT DOCUMENTS

| | | |
|---|---|---|
| 5,944,738 A | 8/1999 | Amplatz et al. |
| 5,954,766 A | 9/1999 | Zadno Azizi et al. |
| 5,957,949 A | 9/1999 | Leonhardt et al. |
| 5,968,068 A | 10/1999 | Dehdashtian et al. |
| 5,980,570 A | 11/1999 | Simpson |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A * | 3/2000 | Williamson et al. .......... 623/2.11 |
| 6,051,104 A | 4/2000 | Oriaran et al. |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,197,143 B1 | 3/2001 | Bodnar |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,270,526 B1 | 8/2001 | Cox |
| 6,277,555 B1 | 8/2001 | Duran et al. |
| 6,299,637 B1 | 10/2001 | Shaolian et al. |
| 6,299,638 B1 * | 10/2001 | Sauter .......................... 623/1.26 |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,312,462 B1 | 11/2001 | McDermott et al. |
| 6,338,735 B1 | 1/2002 | Stevens |
| 6,348,063 B1 | 2/2002 | Yassour et al. |
| 6,350,277 B1 | 2/2002 | Kocur |
| 6,352,554 B2 | 3/2002 | De Paulis |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,402,780 B2 | 6/2002 | Williamson, IV et al. |
| 6,409,750 B1 | 6/2002 | Hyodoh et al. |
| 6,424,885 B1 | 7/2002 | Niemeyer et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,493,608 B1 | 12/2002 | Niemeyer |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,544,285 B1 | 4/2003 | Thubrikar et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,656,219 B1 | 12/2003 | Wiktor |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,684 B1 | 1/2004 | Morley et al. |
| 6,676,698 B2 | 1/2004 | McGuckin, Jr. et al. |
| 6,682,558 B2 | 1/2004 | Tu et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,716,241 B2 * | 4/2004 | Wilder et al. ................ 623/1.24 |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,805,711 B2 | 10/2004 | Quijano et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin, Jr. et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,018,404 B2 | 3/2006 | Holmberg et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,105,016 B2 | 9/2006 | Shiu et al. |
| 7,115,141 B2 | 10/2006 | Menz et al. |
| 7,125,418 B2 | 10/2006 | Duran et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |

(56) References Cited

U.S. PATENT DOCUMENTS

| | | |
|---|---|---|
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,211,107 B2 | 5/2007 | Bruckheimer et al. |
| 7,252,682 B2 | 8/2007 | Seguin |
| 7,255,706 B2 | 8/2007 | Rosengart |
| 7,261,732 B2 | 8/2007 | Justino |
| 7,276,078 B2 | 10/2007 | Spenser et al. |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,329,279 B2 | 2/2008 | Haug et al. |
| 7,335,218 B2 | 2/2008 | Wilson et al. |
| 7,338,520 B2 | 3/2008 | Bailey et al. |
| 7,347,869 B2 | 3/2008 | Hojeibane et al. |
| 7,351,256 B2 | 4/2008 | Hojeibane et al. |
| 7,374,571 B2 | 5/2008 | Pease et al. |
| 7,377,938 B2 | 5/2008 | Sarac et al. |
| 7,377,941 B2 | 5/2008 | Rhee et al. |
| 7,381,218 B2 | 6/2008 | Schreck |
| 7,384,411 B1 | 6/2008 | Condado |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,453,227 B2 | 11/2008 | Prisco et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,534,259 B2 | 5/2009 | Lashinski et al. |
| 7,544,206 B2 | 6/2009 | Cohn |
| 7,547,322 B2 | 6/2009 | Sarac et al. |
| 7,556,645 B2 | 7/2009 | Lashinski et al. |
| 7,556,646 B2 | 7/2009 | Yang et al. |
| 7,569,071 B2 | 8/2009 | Haverkost et al. |
| 7,578,843 B2 | 8/2009 | Shu |
| 7,585,321 B2 | 9/2009 | Cribier |
| 7,591,848 B2 | 9/2009 | Allen |
| 7,618,446 B2 | 11/2009 | Andersen et al. |
| 7,618,447 B2 | 11/2009 | Case et al. |
| 7,682,390 B2 | 3/2010 | Seguin |
| 7,708,775 B2 | 5/2010 | Rowe et al. |
| 7,780,726 B2 | 8/2010 | Seguin |
| 7,785,341 B2 * | 8/2010 | Forster et al. ............ 606/194 |
| 7,806,919 B2 | 10/2010 | Bloom et al. |
| 7,857,845 B2 | 12/2010 | Stacchino et al. |
| 8,211,169 B2 * | 7/2012 | Lane et al. ............ 623/2.1 |
| 8,512,397 B2 * | 8/2013 | Rolando et al. ............ 623/1.26 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0058994 A1 | 5/2002 | Hill et al. |
| 2002/0058995 A1 | 5/2002 | Stevens |
| 2002/0072789 A1 | 6/2002 | Hackett et al. |
| 2002/0095209 A1 | 7/2002 | Zadno Azizi et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0128702 A1 | 9/2002 | Menz et al. |
| 2002/0133183 A1 | 9/2002 | Lentz et al. |
| 2002/0133226 A1 | 9/2002 | Marquez et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0036795 A1 | 2/2003 | Andersen et al. |
| 2003/0040771 A1 | 2/2003 | Hyodoh et al. |
| 2003/0040772 A1 | 2/2003 | Hyodoh et al. |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0163194 A1 | 8/2003 | Quijano et al. |
| 2003/0181850 A1 | 9/2003 | Diamond et al. |
| 2003/0191519 A1 | 10/2003 | Lombardi et al. |
| 2003/0191528 A1 | 10/2003 | Quijano et al. |
| 2003/0199913 A1 | 10/2003 | Dubrul et al. |
| 2003/0199963 A1 | 10/2003 | Tower et al. |
| 2003/0208261 A1 | 11/2003 | Thorpe et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034407 A1 | 2/2004 | Sherry |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0055606 A1 | 3/2004 | Hendricksen et al. |
| 2004/0078072 A1 | 4/2004 | Tu et al. |
| 2004/0078074 A1 | 4/2004 | Anderson et al. |
| 2004/0082904 A1 | 4/2004 | Houde et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093060 A1 | 5/2004 | Seguin et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0127979 A1 | 7/2004 | Wilson et al. |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson et al. |
| 2004/0167620 A1 | 8/2004 | Ortiz et al. |
| 2004/0186558 A1 | 9/2004 | Pavcnik et al. |
| 2004/0186563 A1 | 9/2004 | Lobbi |
| 2004/0193261 A1 | 9/2004 | Berreklouw |
| 2004/0210240 A1 | 10/2004 | Saint |

(56) References Cited

U.S. PATENT DOCUMENTS

| | | |
|---|---|---|
| 2004/0210304 A1 | 10/2004 | Seguin et al. |
| 2004/0210307 A1 | 10/2004 | Khairkhahan |
| 2004/0215333 A1 | 10/2004 | Duran et al. |
| 2004/0215339 A1 | 10/2004 | Drasler et al. |
| 2004/0225353 A1 | 11/2004 | McGuckin et al. |
| 2004/0225354 A1 | 11/2004 | Allen et al. |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060029 A1 | 3/2005 | Le et al. |
| 2005/0060030 A1 | 3/2005 | Lashinski et al. |
| 2005/0075584 A1 | 4/2005 | Cali |
| 2005/0075712 A1 | 4/2005 | Biancucci et al. |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075726 A1 | 4/2005 | Svanidze et al. |
| 2005/0075727 A1 | 4/2005 | Wheatley |
| 2005/0075728 A1 | 4/2005 | Nguyen et al. |
| 2005/0075729 A1 | 4/2005 | Nguyen et al. |
| 2005/0075730 A1 | 4/2005 | Myers et al. |
| 2005/0075731 A1 | 4/2005 | Artof et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0107871 A1 | 5/2005 | Realyvasquez et al. |
| 2005/0113910 A1 | 5/2005 | Paniagua et al. |
| 2005/0119688 A1 | 6/2005 | Bergheim |
| 2005/0131438 A1 | 6/2005 | Cohn |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy et al. |
| 2005/0222674 A1 | 10/2005 | Paine |
| 2005/0222675 A1 | 10/2005 | Sauter |
| 2005/0228495 A1 | 10/2005 | Macoviak |
| 2005/0234546 A1 | 10/2005 | Nugent et al. |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283231 A1* | 12/2005 | Haug et al. .................. 623/2.11 |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0085060 A1* | 4/2006 | Campbell .................... 623/1.26 |
| 2006/0089711 A1 | 4/2006 | Dolan |
| 2006/0095117 A1 | 5/2006 | Popelar et al. |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0190017 A1 | 8/2006 | Cyr et al. |
| 2006/0195134 A1 | 8/2006 | Crittenden |
| 2006/0195184 A1 | 8/2006 | Lane et al. |
| 2006/0206192 A1 | 9/2006 | Tower et al. |
| 2006/0206202 A1 | 9/2006 | Bonhoeffer et al. |
| 2006/0212111 A1 | 9/2006 | Case et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276882 A1 | 12/2006 | Case et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0032850 A1 | 2/2007 | Ruiz et al. |
| 2007/0038295 A1 | 2/2007 | Case et al. |
| 2007/0043431 A1 | 2/2007 | Melsheimer |
| 2007/0043435 A1 | 2/2007 | Seguin et al. |
| 2007/0051377 A1 | 3/2007 | Douk et al. |
| 2007/0073392 A1 | 3/2007 | Heyninck Jantz et al. |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0093890 A1 | 4/2007 | Eliasen et al. |
| 2007/0100432 A1 | 5/2007 | Case et al. |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0106372 A1 | 5/2007 | Osborne et al. |
| 2007/0112415 A1 | 5/2007 | Bartlett |
| 2007/0112422 A1 | 5/2007 | Dehdashtian |
| 2007/0118209 A1 | 5/2007 | Strecker |
| 2007/0118215 A1 | 5/2007 | Moaddeb |
| 2007/0162102 A1 | 7/2007 | Ryan et al. |
| 2007/0162113 A1 | 7/2007 | Sharkawy et al. |
| 2007/0168024 A1 | 7/2007 | Khairkhahan |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |

(56) References Cited

U.S. PATENT DOCUMENTS

| | | |
|---|---|---|
| 2007/0237802 A1 | 10/2007 | McKay |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0260305 A1 | 11/2007 | Drews et al. |
| 2007/0265701 A1 | 11/2007 | Gurskis et al. |
| 2007/0270944 A1 | 11/2007 | Bergheim et al. |
| 2007/0288000 A1 | 12/2007 | Bonan |
| 2007/0293942 A1 | 12/2007 | Mirzaee |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan et al. |
| 2008/0065001 A1 | 3/2008 | DiNucci et al. |
| 2008/0065204 A1 | 3/2008 | Macoviak et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082164 A1 | 4/2008 | Friedman |
| 2008/0082165 A1 | 4/2008 | Wilson et al. |
| 2008/0082166 A1 | 4/2008 | Styrc et al. |
| 2008/0097595 A1 | 4/2008 | Gabbay |
| 2008/0103586 A1 | 5/2008 | Styrc et al. |
| 2008/0125859 A1 | 5/2008 | Salahieh et al. |
| 2008/0133033 A1 | 6/2008 | Wolff et al. |
| 2008/0140189 A1 | 6/2008 | Nguyen et al. |
| 2008/0147105 A1 | 6/2008 | Wilson et al. |
| 2008/0147160 A1 | 6/2008 | Ghione et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188880 A1 | 8/2008 | Fischer et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0249619 A1 | 10/2008 | Stacchino et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0255662 A1 | 10/2008 | Stacchino et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0018570 A1 | 1/2009 | Righini et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0157175 A1 | 6/2009 | Benichou |
| 2009/0164004 A1 | 6/2009 | Cohn |
| 2009/0164006 A1 | 6/2009 | Seguin et al. |
| 2009/0171447 A1 | 7/2009 | Von Segesser et al. |
| 2009/0171456 A1 | 7/2009 | Kveen et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0209955 A1 | 8/2009 | Forster et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0222084 A1 | 9/2009 | Friedman |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0254165 A1 | 10/2009 | Tabor et al. |
| 2009/0287296 A1 | 11/2009 | Manasse |
| 2010/0004740 A1 | 1/2010 | Seguin et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0069852 A1 | 3/2010 | Kelley |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |
| 2010/0274351 A1 | 10/2010 | Rolando et al. |
| 2010/0292782 A1 | 11/2010 | Giannetti et al. |
| 2011/0082539 A1 | 4/2011 | Suri |

FOREIGN PATENT DOCUMENTS

| | | |
|---|---|---|
| DE | 19532846 A1 | 3/1997 |
| DE | 19546692 C2 | 6/1997 |
| DE | 19907646 A1 | 8/2000 |
| DE | 10010074 A1 | 10/2001 |
| DE | 10049812 A1 | 4/2002 |
| DE | 10049813 C1 | 4/2002 |
| DE | 10049815 A1 | 4/2002 |
| DE | 10121210 A1 | 11/2002 |
| DE | 10301026 A1 | 2/2004 |
| DE | 19857887 A1 | 5/2005 |
| EP | 0133420 B1 | 2/1988 |
| EP | 0155245 B1 | 5/1990 |
| EP | 0592410 B1 | 10/1995 |
| EP | 0515324 B1 | 12/1996 |
| EP | 0850607 A1 | 7/1998 |
| EP | 1057460 A1 | 12/2000 |
| EP | 1259194 B1 | 2/2005 |
| EP | 1214020 B1 | 3/2005 |
| EP | 1088529 B1 | 6/2005 |
| EP | 1014896 B1 | 11/2005 |
| EP | 1469797 A1 | 11/2005 |
| EP | 1603493 A2 | 12/2005 |
| EP | 1600127 B1 | 11/2006 |
| EP | 1255510 A1 | 4/2007 |
| EP | 1143882 B1 | 12/2007 |
| EP | 1690515 B1 | 7/2008 |
| EP | 1570809 B1 | 1/2009 |
| EP | 1330213 B1 | 3/2009 |

(56) References Cited

FOREIGN PATENT DOCUMENTS

| | | | |
|---|---|---|---|
| EP | 2047824 A1 | 4/2009 |
| EP | 2055266 A2 | 5/2009 |
| EP | 1370201 B1 | 9/2009 |
| EP | 2119417 A2 | 11/2009 |
| EP | 2133039 A2 | 12/2009 |
| EP | 2246011 A1 | 3/2010 |
| FR | 2788217 A1 | 7/2000 |
| FR | 2815844 A1 | 1/2003 |
| GB | 2056023 A | 8/1983 |
| GB | 2433700 A | 12/2007 |
| NL | 1017275 C2 | 8/2002 |
| SU | 1271508 A1 | 11/1986 |
| WO | WO9529640 A1 | 11/1995 |
| WO | WO9724989 A1 | 7/1997 |
| WO | WO9817202 A1 | 4/1998 |
| WO | WO9829057 A1 | 7/1998 |
| WO | WO9913802 A1 | 3/1999 |
| WO | WO9956665 A1 | 11/1999 |
| WO | WO0041652 A1 | 7/2000 |
| WO | WO0044313 A1 | 8/2000 |
| WO | WO0047136 A1 | 8/2000 |
| WO | WO0047139 A1 | 8/2000 |
| WO | WO0062714 A1 | 10/2000 |
| WO | WO0062716 A1 | 10/2000 |
| WO | WO0121107 A1 | 3/2001 |
| WO | WO0135870 A1 | 5/2001 |
| WO | WO0149213 A2 | 7/2001 |
| WO | WO0154625 A1 | 8/2001 |
| WO | WO0162189 A1 | 8/2001 |
| WO | WO0164137 A1 | 9/2001 |
| WO | WO0176510 A2 | 10/2001 |
| WO | WO0222054 A1 | 3/2002 |
| WO | WO0236048 A1 | 5/2002 |
| WO | WO02041789 A2 | 8/2002 |
| WO | WO02076348 A1 | 10/2002 |
| WO | WO02047575 A2 | 12/2002 |
| WO | WO03003949 A2 | 1/2003 |
| WO | WO03011195 A2 | 2/2003 |
| WO | WO03003943 A2 | 11/2003 |
| WO | WO03094797 A1 | 11/2003 |
| WO | WO2004019825 A1 | 3/2004 |
| WO | WO2004082527 A2 | 9/2004 |
| WO | WO2004089250 A1 | 10/2004 |
| WO | WO2004091455 A2 | 10/2004 |
| WO | WO2005004753 A1 | 1/2005 |
| WO | WO2005046528 A1 | 5/2005 |
| WO | WO2006026371 A1 | 3/2006 |
| WO | WO2006044679 A1 | 4/2006 |
| WO | WO2006086135 A2 | 8/2006 |
| WO | WO2008047354 A2 | 4/2008 |
| WO | WO2008138584 A1 | 11/2008 |
| WO | WO2008150529 A1 | 12/2008 |
| WO | WO2009002548 A1 | 12/2008 |
| WO | WO2009024716 A2 | 2/2009 |
| WO | WO2009029199 A1 | 3/2009 |
| WO | WO2009042196 A2 | 4/2009 |
| WO | WO2009045331 A1 | 4/2009 |
| WO | WO2009045338 A1 | 4/2009 |
| WO | WO2009061389 A2 | 5/2009 |
| WO | WO2009091509 A1 | 7/2009 |
| WO | WO2009094188 A2 | 7/2009 |
| WO | WO2009111241 A2 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. I 664-I 669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al., "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

European Search Report issued in EP App No. 08165227, dated Mar. 13, 2009.

European Search Report issued in EP Application No. 05004289, dated Jun. 2, 2005, 3 pages.

European Search Report issued in EP Application No. 06101425, dated May 3, 2006, 6 pages.

European Search Report issued in EP Application No. 08150075, dated Mar. 27, 2008, 6 pages.

European Search Report issued in EP Application No. 11425310, completed May 31, 2012, 8 pages.

(56) References Cited

OTHER PUBLICATIONS

European Search Report issued in EP Publication No. 1570809 (EP App No. 05004289.4), dated Jan. 5, 2007, 5 pages.
Extended European Search Report issued in EP 09179414, dated Oct. 18, 2010, 8 pages.
Extended European Search Report issued in EP Application 09158822, dated Sep. 29, 2009, 5 pages.
Hanzel, et al., "Complications of percutaneous aortic valve replacement: experience with the CriberEdwardsTm percutaneous heart valve," EuroIntervention Supplements (2006), I (Supplement A) A3-A8.
Huber, et al., "Do Valved Stents Compromise Coronary Flow?" Eur. J. Cardiothorac. Surg. 2004;25:754-759.
International Search Report issued in International Application No. PCT/I B2006/000967, published as WO2006/085225, mailed Jul. 6, 2006.
Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.
Khambadkone, et al, "Percutaneous Implantation of Pulmonary Valves," Expert Review of Cardiovascular Therapy (England), Nov. 2003, pp. 541-548.
Khambadkone, et al, "Percutaneous Pulmonary Valve Implantation: Early and Medium Term Results," Circulation 108 (17 Supplement), Oct. 28, 2003, p. 1V-375.
Khambadkone, et al, "Percutaneous Pulmonary Valve Implantation: Impact of Morphology on Case Selection," Circulation 108 (17 Supplement), Oct. 28, 2003, p. IV-642-IV-643.
Lutter, et al, "Percutaneous Aortic Valve Replacement: An Experimental Study. I. Studies on Implantation," The Journal of Thoracic and Cardiovascular Surgery, Apr. 2002, pp. 768-776.
Lutter, et al, "Percutaneous Valve Replacement: Current State and Future Prospects," Annals of Thoracic Surgery (Netherlands), Dec. 2004, pp. 2199-2206.
Ma, Ling, et al., "Double-crowned valved stents for off-pump mitral valve replacement," European Journal of Cardio Thoracic Surgery, 28:194-198, 2005.
Medtech Insight, "New Frontiers in Heart Valve Disease," vol. 7, No. 8 (2005).
Palacios, "Percutaneous Valve Replacement and Repair, Fiction or Reality?" Journal of American College of Cardiology, vol. 44, No. 8 (2004) pp. 1662-1663.
Pavcnik et al., "Aortic and venous valve for percutaneous insertion," Min. Invas. Ther. & Allied Techol. 2000, vol. 9, pas. 287-292.
Pelton et al., "Medical Uses of Nitinol," Materials Science Forum vols. 327-328, pp. 63-70 (2000).
Ruiz, "Transcathether Aortic Valve Implantation and Mitral Valve Repair: State of the Art," Pediatric Cardiology, vol. 26, No. 3 (2005).
Saliba, et al, "Treatment of Obstructions of Prosthetic Conduits by Percutaneous Implantation of Stents," Archives des Maldies du Coeur et des Vaisseaux (France), 1999, pp. 591-596.
Stassano et al., "Mid-term results of the valve-on-valve technique for bioprosthetic failure," Eur. J. Cardiothorac. Surg. 2000; 18:453-457.
Webb, et al., "Percutaneous Aortic Valve Implantation Retrograde from the Femoral Artery," Circulation (2006), 1 13;842-850.
International Search Report issued in PCT/IB2012/057598, mailed Apr. 10, 2013, 6 pagaes.

* cited by examiner

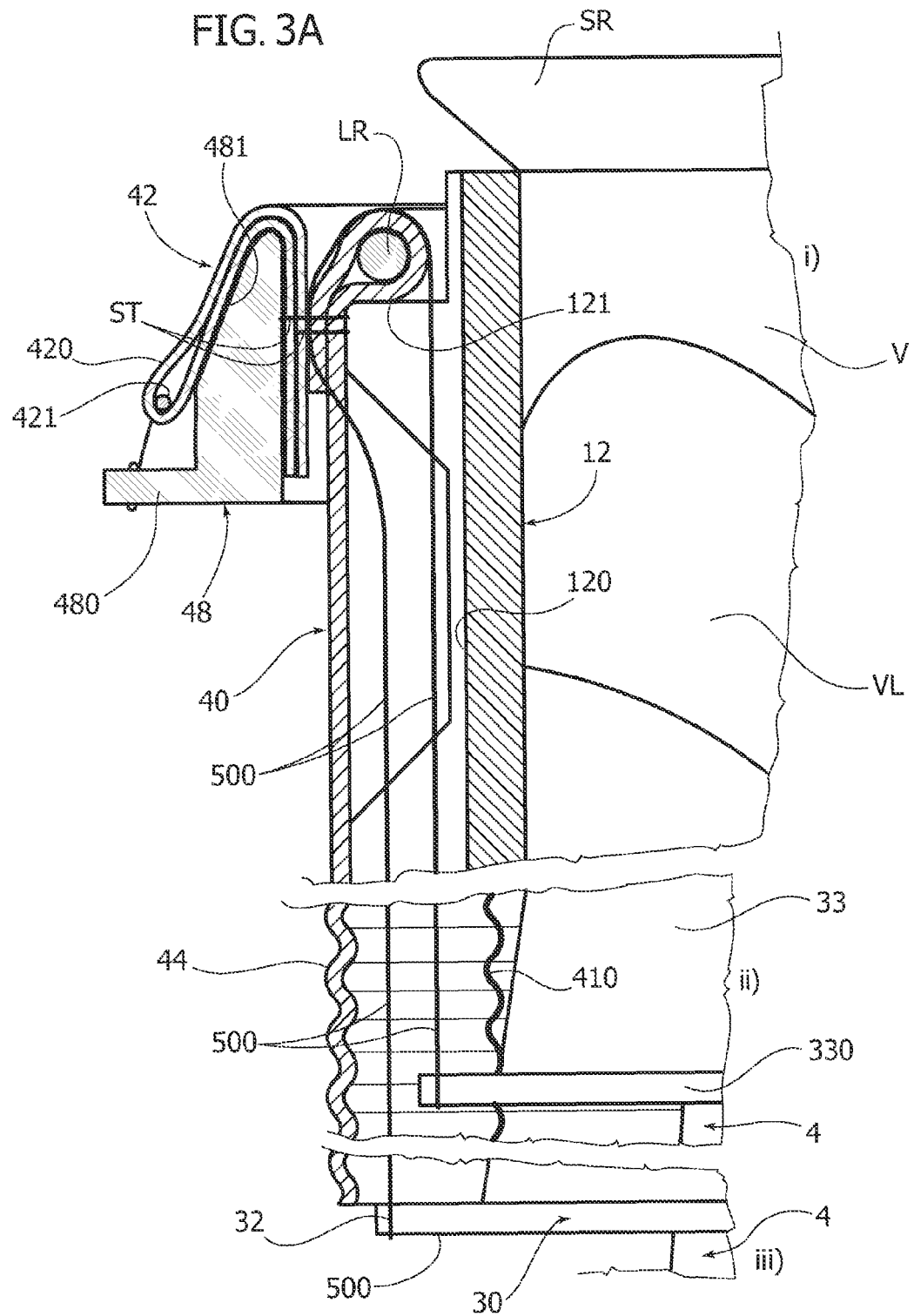

PROSTHETIC VASCULAR CONDUIT AND ASSEMBLY METHOD

CROSS-REFERENCE TO RELATED APPLICATION

This application claims priority under §119 to European patent application EP 11425310.7, filed on Dec. 29, 2011, the content of which is incorporated herein by reference in its entirety.

TECHNICAL FIELD

The present disclosure relates to prosthetic vascular conduits or grafts and kits for the implantation thereof. Various embodiments may relate to kits for implanting prosthetic vascular conduits adapted to couple with an associated valve for controlling blood flow through the conduit.

BACKGROUND

Valved conduits or grafts, which are arrangements including a prosthetic vascular conduit with an associated prosthetic valve to control flow of blood through the conduit, may be used for various purposes including, for example, the replacement of the aortic valve in conjunction with the ascending aorta. The aorta is the largest blood vessel in the human body, carrying blood from the left ventricle of the heart throughout the body. The ascending aorta is the first section of the aorta, which stems from the left ventricle and extends to the aortic arch. The aortic valve is located at the root of the ascending aorta and controls the blood flow by permitting blood to flow from the left ventricle into the ascending aorta while preventing or restricting blood flow in the opposite direction. The coronary arteries, which supply blood to the heart muscle itself, branch from the ascending aorta. Downstream of the aortic valve, the wall of the ascending aorta exhibits three outward protrusions approximately spaced 120 degrees apart. These protrusions are known as the Valsalva sinuses. For replacement of the aortic valve and the ascending aorta, the valve in the valved conduit is arranged at one end of the prosthetic vascular conduit with its leaflets oriented to permit blood flow from the left ventricle into the conduit, while preventing blood flow out of the conduit in the opposite direction.

Practitioners may prefer having the option of coupling the valve to the conduit just before the replacement procedure. In some cases, for example, practitioners wish to couple the valve to the conduit, possibly in the operating room, only after the specific requirements (e.g., anatomy and pathology) of the patient are known. The coupling of the valve to the conduit and the subsequent implantation of the assembly may be important steps in any vascular surgery intervention. Practitioners are striving for reducing the overall time required for implanting a vascular prosthesis such as a prosthetic conduit, as saving time reduces the risk for the patient.

SUMMARY

Exemplary embodiments herein refer to a kit for the implantation of a prosthetic vascular conduit including:
  a prosthetic vascular conduit for coupling to a prosthetic valve having an annular portion, the prosthetic vascular conduit including a terminal collar member configured for receiving the annular portion of the valve, wherein the terminal collar member includes a cuff which is radially contractible to engage the annular portion of the valve to couple the valve to the conduit,
  a holder device including a shaft and a hub located at an end of a proximal portion of the shaft, the hub including a receiving portion configured for housing a prosthetic valve, wherein the prosthetic vascular conduit is fitted on the holder device so that at least a portion of the conduit adjacent to the cuff wraps the receiving portion of the hub,
  a sleeve member fitted onto the conduit in a position corresponding to the receiving portion of the hub, wherein the cuff is wrapped on the sleeve member, and wherein the sleeve member is slidable away from the hub to unwrap the cuff around the annular portion of a prosthetic valve housed within the receiving portion of the hub.

Exemplary embodiments herein may relate to a method of making a prosthetic valved conduit, the method including:
  providing a kit according to exemplary embodiments of the invention;
  providing a prosthetic heart valve having an annular portion;
  advancing the heart valve prosthesis into the receiving portion of the hub until the annular portion of the prosthetic heart valve contacts the receiving portion;
  sliding the sleeve member away from the hub to unwrap the cuff of the prosthetic vascular conduit around the annular portion of the prosthetic heart valve, and
  wrapping the cuff of the prosthetic vascular conduit over the annular portion of the prosthetic heart valve by providing a radial contraction of the cuff.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE FIGURES

FIGS. 3 to 8 are exemplary of a sequence of coupling a prosthetic valve with the prosthetic vascular conduit and implanting the prosthetic vascular conduit and the heart valve at an implantation site as described herein, wherein FIGS. 5A, 6A, 7A are views according to the arrows V', VI and VII of FIGS. 5, 6, 7 respectively, wherein FIGS. 7-7A-8 illustrate an exemplary implantation sequence, and wherein FIG. 3A is an enlarged sectional view of details according to various embodiments and indicated by the arrows i), ii) and iii) in FIG. 3.

DETAILED DESCRIPTION

In the following description, numerous specific details are given to provide a thorough understanding of embodiments. The embodiments can be practiced without one or more of the specific details, or with other methods, components, materials, etc. Reference throughout this specification to "one embodiment," "an embodiment," "exemplary embodiment," or "various embodiments" means that a particular feature, structure, or characteristic described in connection with the embodiment is included in at least one embodiment. Thus, the use of these phrases throughout this specification is not necessarily intended to refer to the same embodiment. Furthermore, the particular features, structures, or characteristics may be combined in any suitable manner in one or more embodiments.

Figure 1:
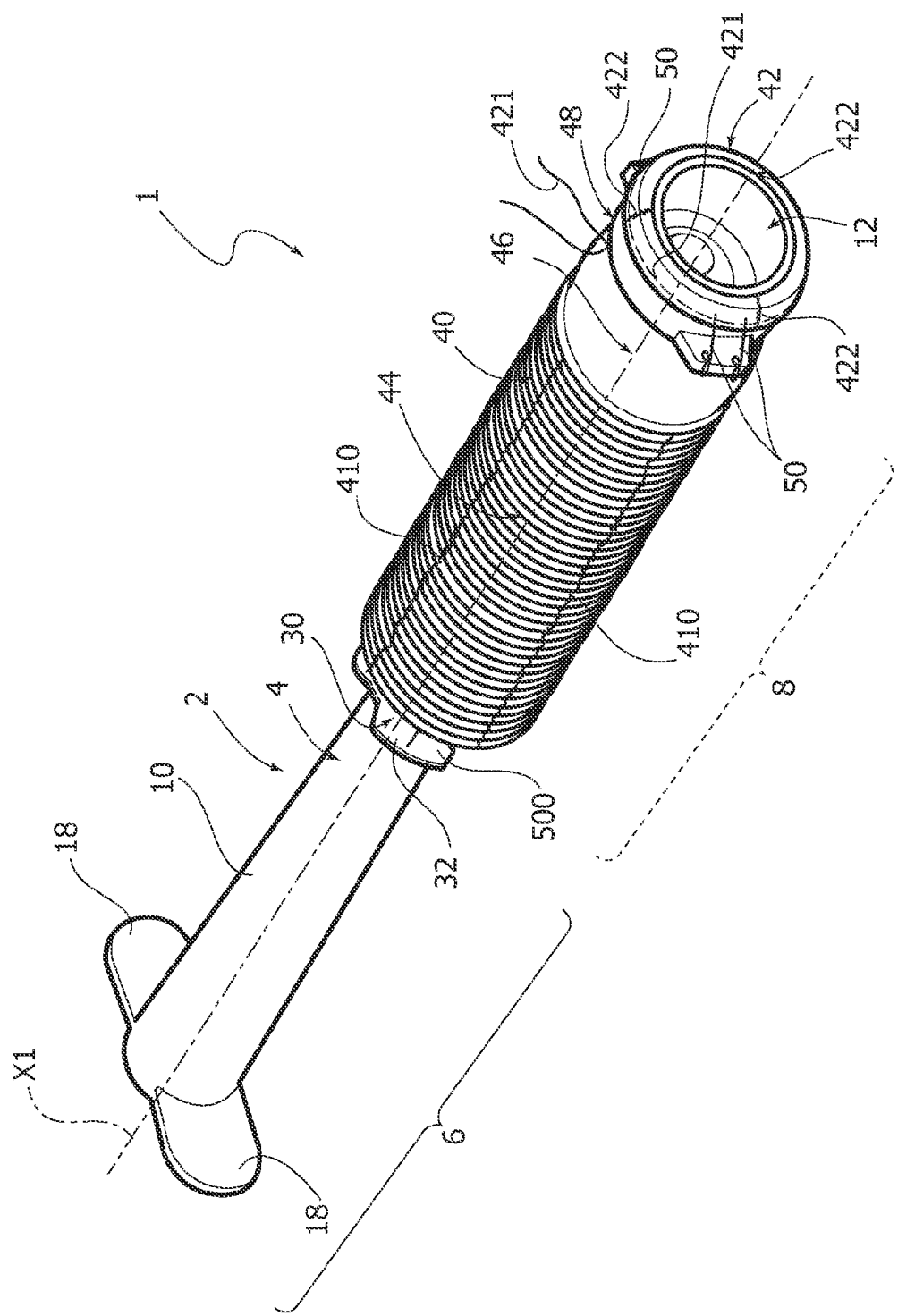
FIG. 1 is an exemplary view of a kit including a prosthetic vascular conduit and a holder device as described herein.
Figure 2:
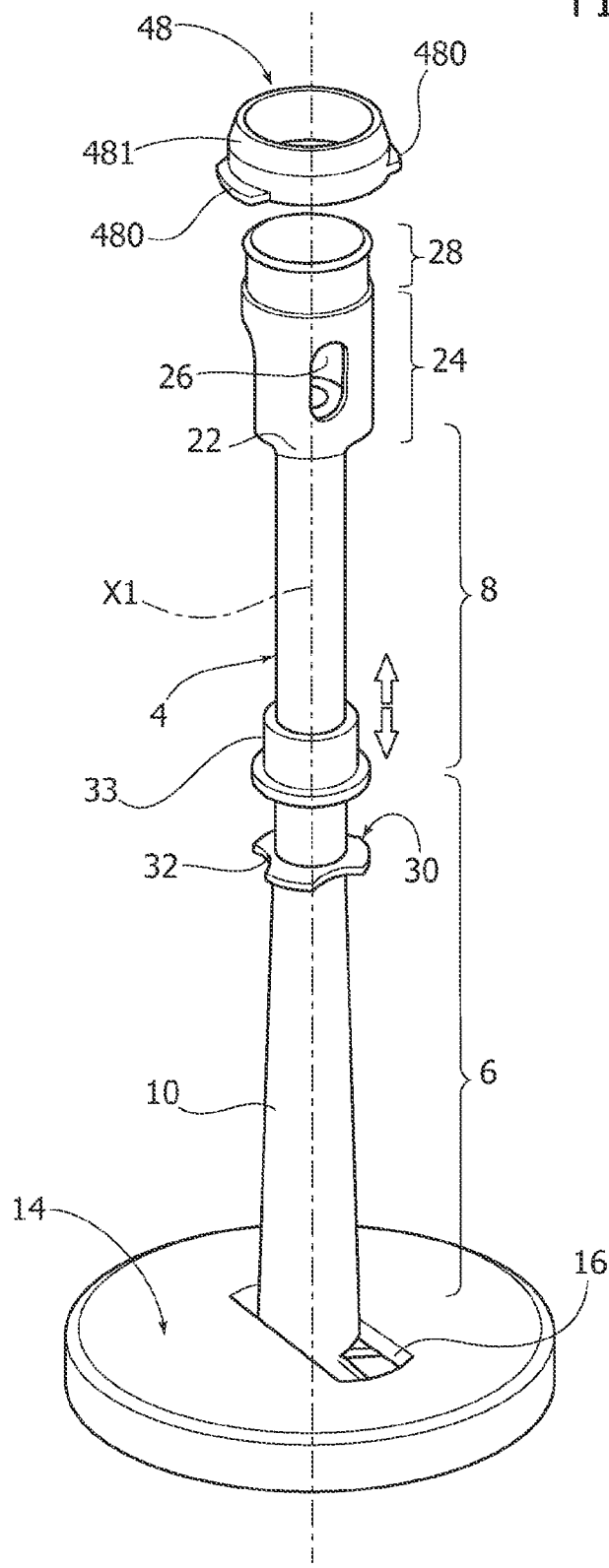
FIG. 2 is a perspective view of the holder device of the kit shown in FIG. 1, without the prosthetic vascular conduit mounted thereon.

With reference to FIGS. 1 and 2, reference 1 designates as a whole a kit for the implantation of a prosthetic vascular conduit according to various embodiments. In various embodiments, the kit may include a delivery tool or holder device 2 including a shaft 4 having a distal portion 6 and a proximal portion 8, wherein the shaft includes a handle 10 provided at the distal portion and a hub 12 coupled at an end of the proximal portion 8. In this description the terms "proximal" and "distal" are used with reference to the implantation site. By way of example, portions of the holder device 2 intended to operate in the proximity of the heart or at an implantation site will be referred to as "proximal," while portions intended to operate away from the heart, for instance the handle 4 which may be in the hand(s) of a practitioner, will be referred to as "distal."

In various embodiments, as shown for example in FIG. 2, the kit 1 may be used in conjunction with a base member 14 including a slot 16 configured for receiving the distal portion of the holder device 2. In particular, in various embodiments (and furthermore with the support of FIG. 3), the shaft 4 may be provided, at one end of the distal portion, with a pair of radially protruding tabs 18. In various exemplary embodiments, the tabs 18 are spaced by about 180 degrees.

Figure 3:
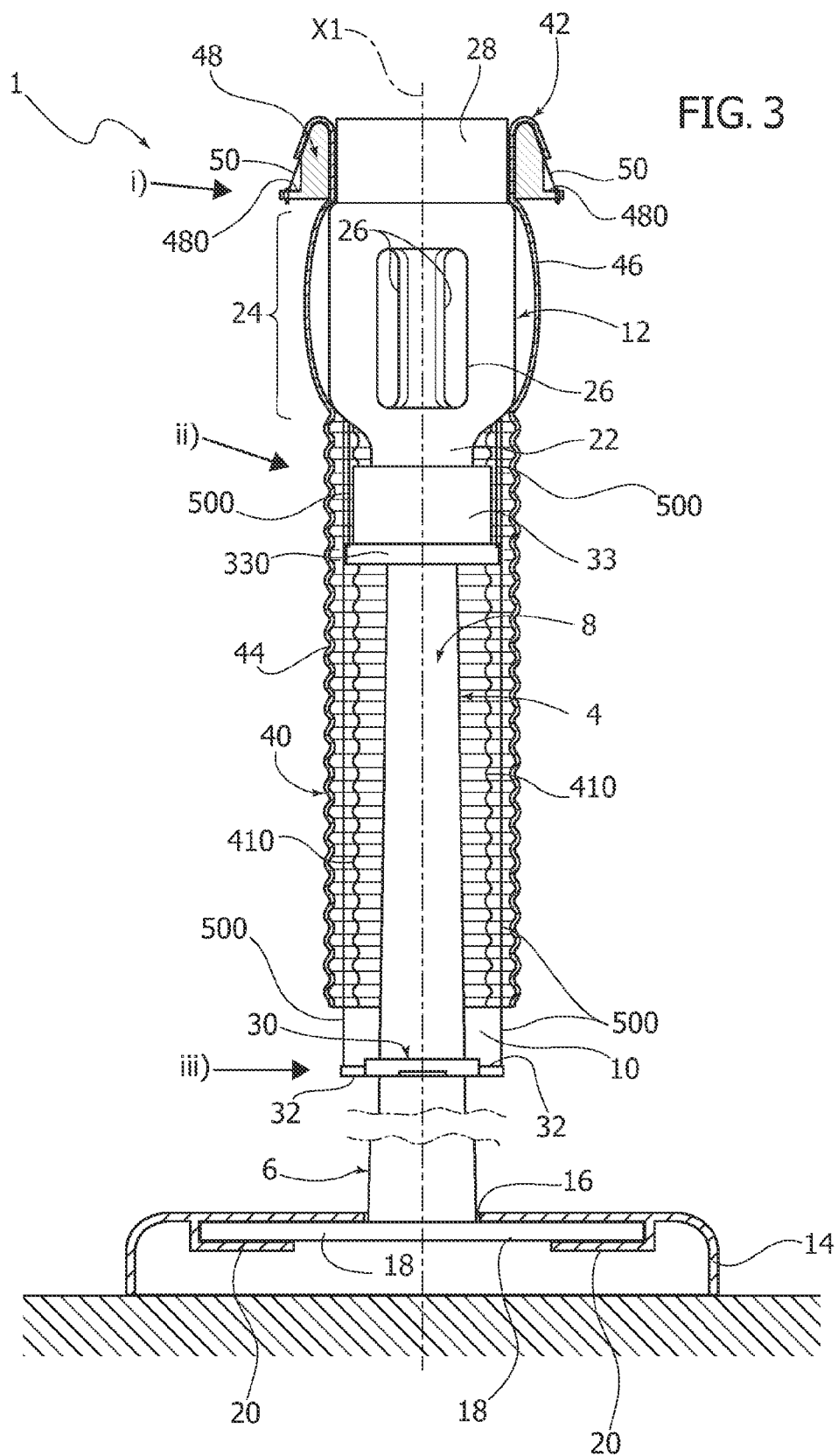

The slot 16 may have a sufficient length and width in order for the tabs 18 to pass through, so that the shaft 4 can be rigidly coupled with the base member 14 by rotating the former after inserting the tabs 18 in the slot 16, thereby sliding the tabs 18 into corresponding bayonet fittings 20, which may be integral with the base member 14 (see, for example, FIG. 3). Several connecting means other than the bayonet coupling herein described may be used for coupling the shaft to the base member, e.g. releasable snap fittings. Coupling the shaft 4 to the base member 14 may render the holder device 2 self standing, as further described below.

In various embodiments, the hub 12 may be designed for receiving a prosthetic valve. In various embodiments, as shown for example in FIG. 2, the hub 12 may be substantially cup shaped and include:
- a first end portion with a coupling collar 22 adapted to be fitted at the end of the proximal portion 8,
- a cylindrical portion 24 having three windows 26 (which may e.g. be spaced 120 degrees apart), and
- a second end portion having a receiving member, e.g. a receiving collar 28, configured for serving as a temporary valve housing.

In various embodiments, at an intermediate position (e.g. substantially halfway along the shaft 4) a ring member 30 may be provided rigidly connected to the shaft 4 and which, in various embodiments, may exhibit radial protrusions 32, for example in the form of fingers or tabs. In various embodiments the protrusions 32 may be provided in the number of two (spaced 180 degrees) or three (spaced 120 degrees).

In various embodiments, a bushing 33 may be fitted onto the shaft 4 at a position between the ring member 30 and the hub 12. The bushing 33 may be slidable along the shaft 4 and in various embodiments may be provided with a flange 330.

In various embodiments, the components of the holder device 2 may be mounted coaxially to a longitudinal axis X1 of the holder device 2, As will be apparent from the following description, in various embodiments this may coincide with a longitudinal axis of a prosthetic vascular conduit coupled to the holder device 2.

In the figures, reference 40 denotes, as a whole, a prosthetic vascular conduit intended to be coupled with a prosthetic heart valve V to produce a so-called valved conduit or valve graft. Such a valved conduit may be used for replacing a native heart valve and an associated blood vessel in a patient. The aortic valve and the ascending aorta are one non-limiting examples of such a valve and an associated blood vessel. The pulmonary valve and the pulmonary artery may be other examples.

The valve V may be any type of valve adapted for replacement of a native heart valve in a patient. In various embodiments, the valve V may be a mechanical prosthetic heart valve. In various embodiments, such as those shown herein, the valve V may be a biological heart valve. Biological valves can be produced from animal tissues (e.g., bovine or porcine pericardium) cut, shaped and assembled (e.g., by stitching) to produce the desired valve structure. Valves for replacing a native heart valve can also be native valves derived from animals and treated to avoid degradation and adverse effects when implanted into the human body. So-called "porcine" valves obtained from native valves explanted from pigs are exemplary of this type of valves.

In various embodiments, the valve V may include a rigid or semi-rigid stent or be a so-called "stentless" type. An exemplary valve suited for use in the arrangement described herein may be a valve as disclosed in U.S. Pat. No. 5,713,953, including a base annular structure including a sewing ring 14, similar to the annulus of the native valve being replaced. In various embodiments (see e.g. FIG. 4), the sewing ring SR may exhibit a(n) (outwardly) flared shape.

In the exemplary embodiments shown, the valve V is associated with the conduit 40 in such a way that the valve leaflets (schematically indicated as VL) may control flow of blood through the conduit by permitting blood flow into the conduit 40 (i.e., blood flow into the aorta, when the conduit 40 is used for aortic replacement) while preventing (or restricting) flow of blood out of the conduit in the opposite direction (i.e., back into the left ventricle of the patient when used for aortic replacement). A reverse arrangement or orientation of the valve V is also possible.

As shown for example in FIGS. 1 and 2, the conduit 40 may include a terminal collar member 42 configured for receiving the annular portion, particularly the sewing ring SR, of the valve V. the collar member 42 includes a cuff 420 located at an end portion thereof and of the conduit 40, the cuff 420 being configured for the coupling of the valve V to the conduit 40.

In various embodiments, the sewing ring SR of the valve V may include a biocompatible textile material (e.g., PET such as Dacron®) and/or animal tissue (e.g., bovine or porcine pericardium) treated to be biocompatible. In various exemplary embodiments, the valve V is anchored to the conduit 40 by stitching (i.e., suturing) performed by a practitioner by taking advantage of both the sewing ring SR of the valve V and the cuff 420 being adapted to be traversed by a suturing material to produce suturing stitches.

In other exemplary embodiments, the conduit 40 includes a tubular textile structure. In various embodiments, the conduit 40 may have a length ranging from 2 centimeters to 10-12 centimeters, with a body portion 44 including a tubular wall of a textile material, such as PET (Dacron®). In various embodiments, the body portion 44 is in the form of a corrugated (i.e., crimped or grooved) structure providing longitudinal flexibility and radial compressibility, while ensuring that the conduit will not unduly radially expand under the pressure of blood flowing therethrough. In various embodiments, the body portion 44 may include a collagen-impregnated woven Dacron® graft. According to other embodiments, the body portion 44 is made from other structures well known in the area of vascular grafts.

In various embodiments used for replacing the ascending aorta, the conduit 40 may also include an intermediate portion 46 located between the body portion 44 and the terminal collar member 42. The intermediate portion 46 may include a material adapted to permit a radial expansion of the conduit wall into the Valsalva sinuses located immediately downstream of the aortic valve. Such a radial resiliency may be due to the intermediate portion 46 being made of a textile material having a stitching pattern such as to bestow on the resulting fabric a certain degree of resiliency. In various embodiments, the intermediate portion 46 may be pre-formed or fabricated to have a size and shape adapted to substantially mimic or replicate the shape of the native Valsalva sinus.

In various embodiments, one or both of the body portion 44 and the intermediate portion 46 of the conduit may be punctured or cut to open passages therein for connection of the coronary ostia.

In various embodiments, the cuff 420 (and the terminal collar member as well) may also similarly exhibit a certain degree of radial resiliency (i.e., expandability), possibly starting from an initial rest (i.e., unbiased or not expanded) condition where the terminal collar member 42 may have, at least marginally, a smaller diameter than the rest of the conduit 40. The terminal collar member 42 may include a textile material (e.g., knitted Dacron® thread) connected to the intermediate portion 46 to produce a radially expandable terminal portion of the conduit 40.

In various embodiments, the terminal collar member 42 may be a separate element (e.g., formed from a separate piece of material) from the body portion 44 and/or the intermediate portion 46. Connection of the terminal collar member 42 to the intermediate portion 46, as well as connection of the intermediate portion 46 to the body portion 44 or connection of the terminal collar member 42 to the body portion 44 (in embodiments not including the intermediate portion 46) may be achieved by any method or technique known in the art. In various exemplary embodiments, connection may be by one or more of knitting, stitching, or gluing.

In various embodiments, the body portion 44, the intermediate portion 46 and the terminal collar member 42 may be a single piece of material. For example, different sections of a same body including different knitting or stitching patterns. In various embodiments, the intermediate portion 46 can be dispensed with, whereby the terminal collar member 42 is directly connected to the body portion 44 by any of the techniques considered.

The terminal collar member 42 may be intended to accommodate the valve V to permit easy, fast and reliable coupling and subsequent anchoring of the valve V to the conduit 40. In exemplary embodiments, the cuff 420 may be intended to accommodate the annular portion of the valve V, namely the sewing ring SR.

In various embodiments, the terminal collar member 42, in particular the cuff 420, may be radially contractible (i.e., shrinkable). Radial contraction of the terminal collar member 42 may be due to inherent contractibility and/or be achieved via a positive contracting action. Elastic contractibility is exemplary of inherent contractibility. Elastic contractibility of the cuff 420 may be achieved via an elastically contractible member such as an elastic ring of a plastics material, a metallic ring (e.g., superelastic metallic alloys such as Nitinol), or an open, radially contractible ring of a rigid or semi-rigid material such as a metal or plastics material.

Radial contraction achieved via a positive contracting action may include shape memory (e.g., of a metallic member) or loop or a slip-knot (to be actuated by the practitioner) formed of a wire-like element such as suturing wire or a thread as used for manufacturing the conduit 40. In an exemplary embodiment as shown in the Figures, the cuff 420 may be made radially contractible by means of a purse-string design, i.e. a drawstring 421 passes through the cuff 420 in and out along a marginal edge thereof, so that upon pulling the drawstring 421 the diameter of the cuff 420 is reduced.

With reference to FIGS. 1 and 3, in various embodiments of the kit 1 the prosthetic vascular conduit 40 may be pre-mounted on the holder device 2 coaxially to the axis X1 and anchored thereto and to a sleeve member 48, as further described below. The sleeve member 48 may include either a flange or a pair of protruding tabs 480 and a tapered end portion 481.

FIG. 1 in particular shows an example of the kit 1 in an assembled configuration, ready for packaging (or for use in the operational theatre). More in detail, the conduit 40 may be fitted onto the holder device 2 so that the body portion 44 substantially surrounds the portion of the shaft 4 included between the ring member 30 and the hub 12 (or even a portion of the hub 12), while on the opposite end, at least a portion of the conduit adjacent to the cuff 420 may wrap around (or encircle) the receiving collar 28. Depending on the actual size and shape of the conduit and the hub 12, the receiving collar 28 may be wrapped (or encircled) by a portion of the conduit located across the interface between the intermediate portion 46 and the collar member 42 or, if the former is not present, between the body portion 44 and the collar member 42.

The sleeve member 48 may be fitted onto the conduit 40 in a position corresponding to the receiving collar 28 of the hub 12. The inner diameter of the sleeve member 48 may be sized and dimensioned to accommodate the conduit 40 and the receiving collar 28. Therefore, in various embodiments the inner diameter of the sleeve member 48 may exceed the external diameter of the receiving collar 28 by substantially twice the wall thickness of the conduit 40. In other embodiments the size of the inner diameter of the sleeve member may be different, in particular smaller, depending on the amount of radial contraction which is tolerated for the conduit 40.

A portion of the terminal collar member 42 adjacent to the cuff 420 and at least a stretch of the intermediate portion 46 (or the body portion 44, in case the intermediate portion 46 is not present) may thus be constrained between the sleeve member 48 and the receiving collar 28, as shown by way of example in FIG. 3.

Furthermore, the cuff 420 may be wrapped (or folded) over some or all of the outer surface of the sleeve member 48. In various embodiments the cuff 420 extends (or wraps) over at least the tapered end portion 481 of the sleeve member 48. Such arrangement can be obtained by up-turning the marginal edge of the cuff 420 on the sleeve member 48. In various embodiments, a first set of anchoring threads 50 may be passed through the cuff 420 and anchored on the sleeve member 48, particularly on the tabs 480 which may be provided with holes or grooves for receiving the threads 50. In exemplary embodiments, the set 50 includes two pairs of anchoring threads (or two single anchoring threads) spaced 180 degrees.

In various embodiments, with reference to FIG. 3A, a second set of anchoring threads 500 may be used to anchor the conduit 40 to the holder device 2. More particularly, in various embodiments a first end of an anchoring thread 500 may be connected (e.g. tied or otherwise fastened) to the flange 330 of the bushing 33. The anchoring thread 500 may then be routed—within the conduit 40—towards the hub 12 whereon a corresponding axial groove 120 may be provided. The thread 500 may thus traverse the groove 120 until it emerges from the interior of the conduit 40 and may be bent in a loop which is external with respect to the conduit and may be made to traverse the conduit 40 (e.g. in a position corresponding to the collar member 42), thereby returning inside the conduit itself.

With reference again to FIG. 3A, in one embodiment the hub 12 may be provided with radially protruding formations 121 which may offer an axial abutment surface to a locking ring LR provided within the body portion 44 (the intermediate portion 46 if present) at a position corresponding to the collar member 42. In various embodiments the locking ring LR may be an elastic ring having an undeformed diameter which is less than the outermost diameter of the hub 12 defined by the formations 121. The anchoring thread 500 may thus be bent in a loop around the locking ring LR, which in turn may bear upon the radially protruding formation 121.

The thread 500 may then be routed again along the groove 120 and towards the ring member 30, whereon a second end of the thread 500 is secured (e.g. tied or otherwise fastened), for instance to the tabs 32. The location of the ring member 30 along the shaft 4 may therefore be mainly dictated by the actual length of the conduit 40.

In various embodiments, the collar member 42 may be provided as a separate piece and may be stitched, for instance by means of stitches ST, to a free proximal end of the body portion 44 (the intermediate portion 46 if present), which in turn may be wrapped around the lock ring LR (thereby defining an annular pocket). In various embodiments the collar member 42 may itself be folded to form a pocket for the drawstring 421. In one embodiment, the stitches ST may traverse both the collar member 42 and the proximal end of the body portion 44 (the intermediate portion 46 if present), thereby securing the former and the latter together to form the conduit 40.

In various embodiments, the bushing 33 is slidable along the shaft 4 and the second end of each thread 500 may be drawn distally before being anchored to the ring member 30, so that the bushing 33 is made to slide along the shaft 4. In order to ensure a proper tensioning of the threads 500, the latter may be secured to the ring member 30 when the bushing 33 has come into contact with the hub 12 (see FIG. 3, for example).

In other embodiments the bushing may be fixedly coupled with the shaft 4, so that no sliding thereof will occur in when the second ends of the threads 500 are drawn prior to anchoring to the ring member 30.

In various embodiments, the threads 500 may includes two anchoring threads spaced (e.g., 180 degrees) apart or three anchoring threads spaced (e.g., 120 degrees) apart. The number of the grooves 120 may thus vary accordingly, preferably envisaging one groove 120 for each set of threads 500.

FIGS. 3 to 6 illustrate an exemplary sequence of coupling and anchoring the valve V to the conduit 40 pre-mounted on the holder device 2. In various embodiments (e.g. with reference to FIGS. 7-8) the holder device 2 may serve as a delivery tool for the prosthetic vascular conduit 40.

Figure 4:
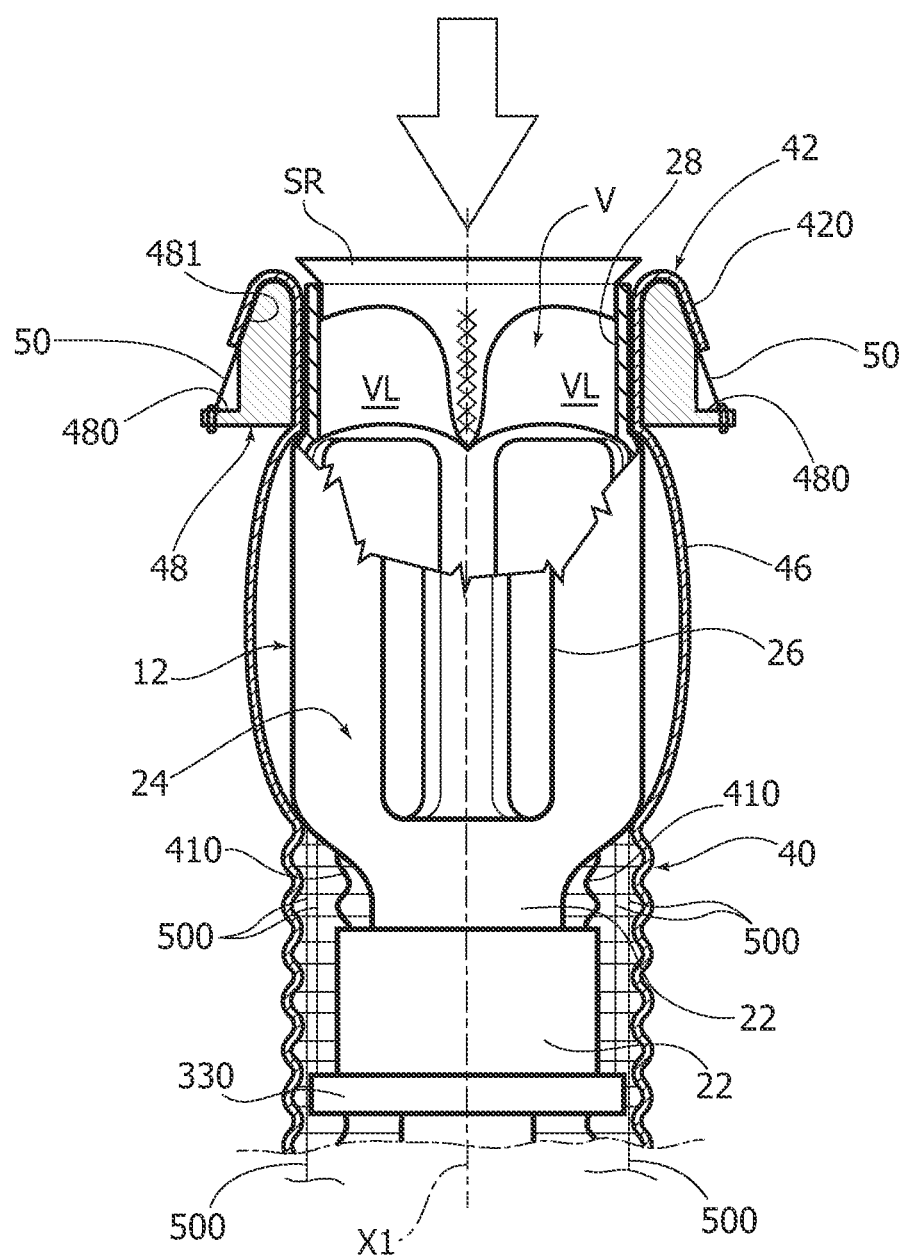

With reference to FIGS. 3 and 4, an operator, assisting the practitioner performing the implantation of a valved conduit in a patient, may couple the holder 2 to the base member 14 as previously described and arrange the assembly on a flat surface. The base member 14, as described, will render the holder 2 with the attached conduit 40 self-standing, so that it will stand in a substantially vertical position. In various embodiments, the base member may be provided as a separate item (i.e. in a different package), because it is made as a standard component, while the holder 2—in particular the receiving collar 28 and the whole hub 12—and the conduit 40 may be manufactured according to the specific sizes required by the patient. In other words, the receiving collar and the prosthetic valve intended to be received therein and coupled to the conduit 40 may have a diameter which is adapted to or optimized for the patient's anatomy.

In various embodiments, the prosthetic heart valve V, exemplified in the figures as a biological valve, may be preferably rinsed in a physiological solution before being coupled to the conduit. The valve V may then be inserted into the receiving collar 28 as shown in FIG. 4, so that the valve leaflets VL will face the interior of the hub 12 with the sewing ring SR contacting the marginal edge of the receiving collar 28.

In various embodiments, the sewing ring SR of the prosthetic valve V may be flared and/or have a maximum diameter which is slightly larger than the inner diameter of the receiving collar 28, so that the sewing ring abuts against the receiving collar 28 preventing the valve V from being pushed far too deep within the hub 12.

During this step, the hub 12 may serve both as a receiving means and a centering means for the valve V. Angular markers 410 (e.g., in the form of lines of contrasting color) can be provided in the wall of the conduit 40 to act as angular references in orienting the valve V with respect to the conduit 10. In addition or alternatively thereto, angular markers 422 (FIG. 1) can be provided in the cuff 42 to act as angular references in orienting the valve V with respect to the cuff 42.

The operator may then cut the anchoring threads 50, thereby removing the constraint which secures the cuff 42 to the sleeve member 48. In embodiments where the cuff 420 is provided with a certain degree of resiliency, the threads 50 may be tensioned to the extent that they slightly stretch the cuff, so that, with the threads cut, the cuff may return to an undeformed condition away from the cutting tool sharp edges, thereby minimizing the risks of accidental damage to the cuff.

Figure 5:
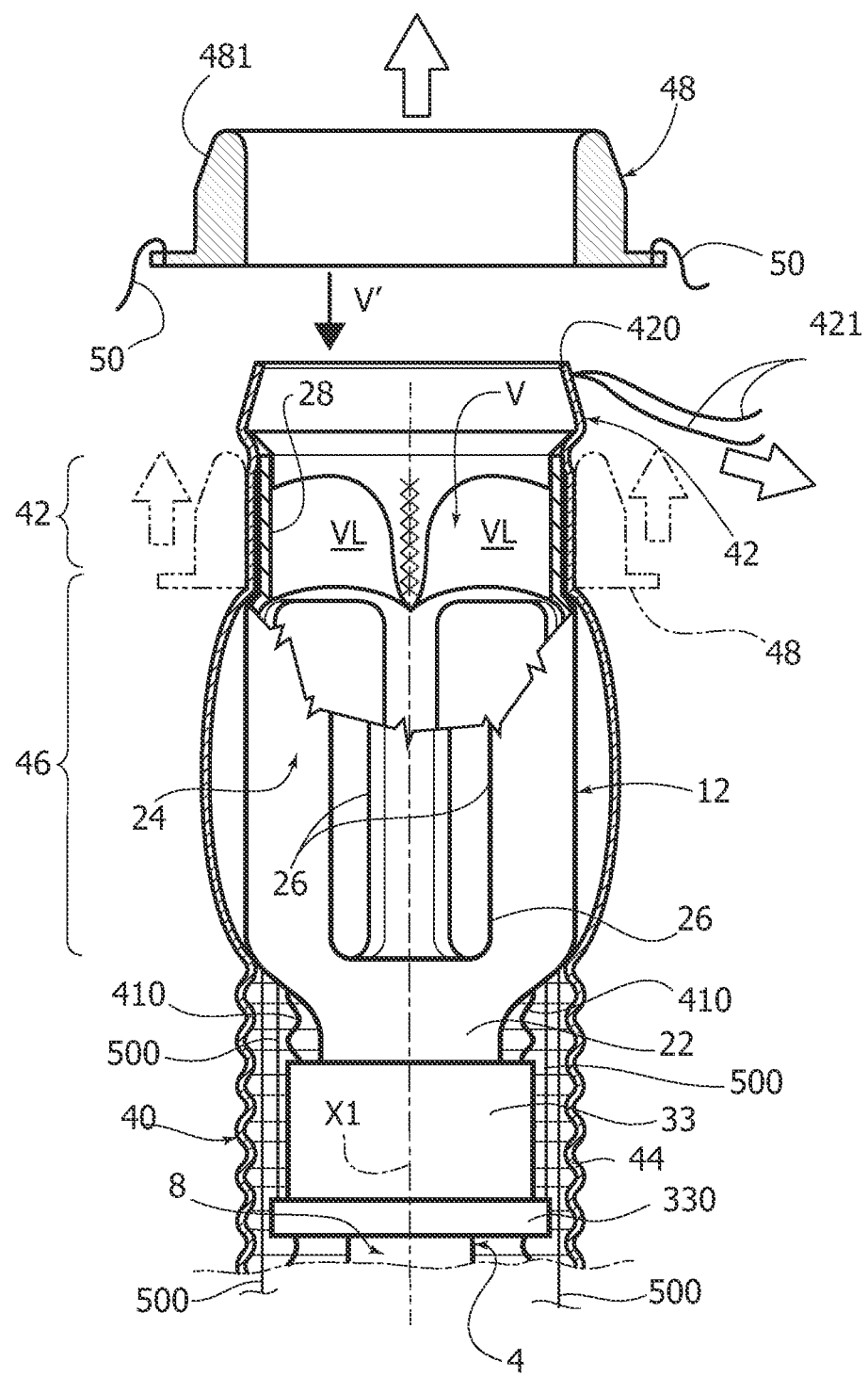
Figure 5A:
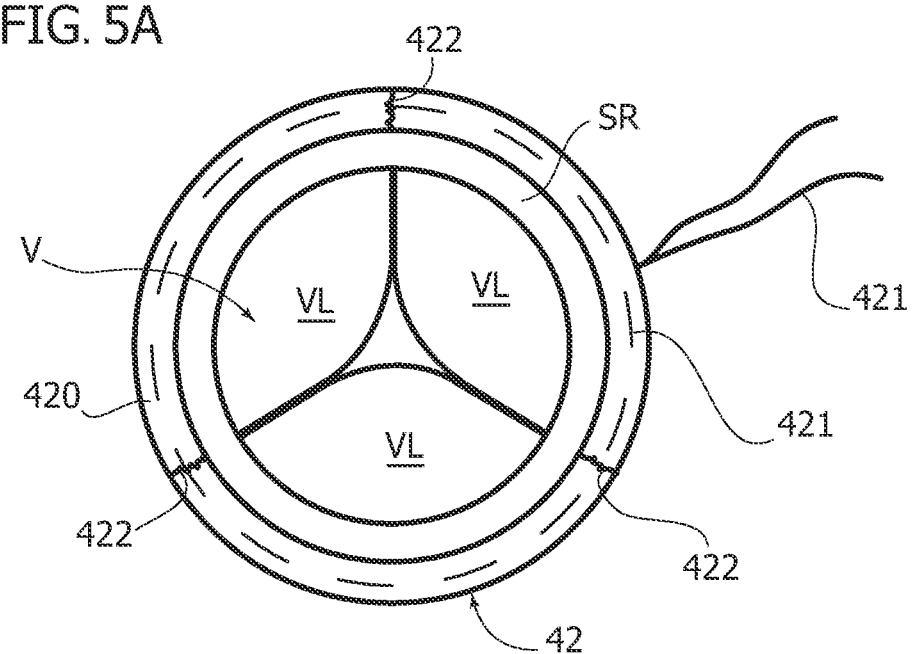

With reference to FIG. 5, the operator may now be able to proceed and slide the sleeve member 48 (axially with reference to the axis X1) away from the hub 12 and the conduit 40, thereby unwrapping (or unfolding) the cuff 420, previously wrapped (or folded) thereon, such that is wraps around (or encircles) the annular portion—and in particular the sewing ring SR—of the valve V. FIGS. 5 and 5A provide a schematic view of a possible configuration of the unwrapped (or unfolded) cuff 420. The sewing ring SR is then laterally surrounded by the cuff 420, with a proximal edge of the cuff 420 extending slightly above a proximal surface of the sewing ring SR.

Figure 6:
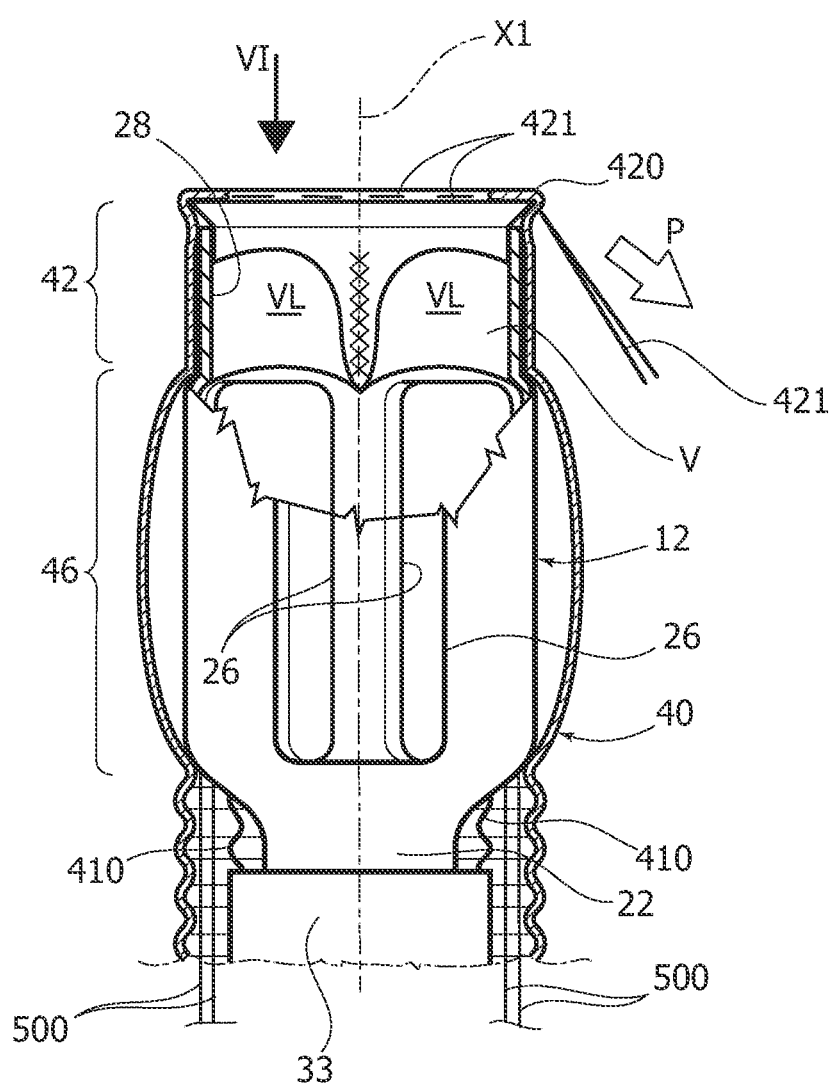
Figure 6A:
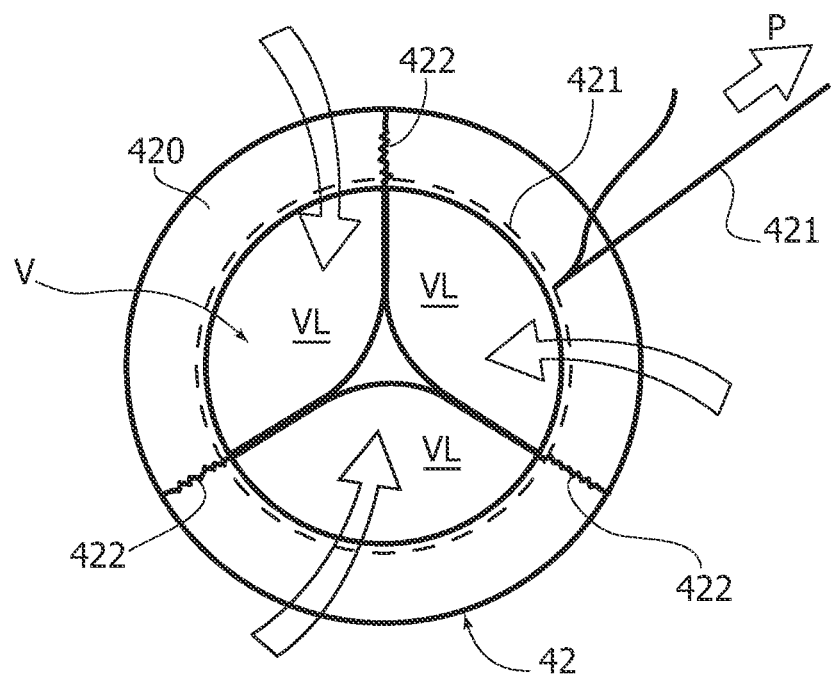

A next step is depicted in FIGS. 6 and 6A. In various embodiments, the purse string design of the cuff 420 may permit an easy and rapid coupling of the valve V to the conduit 40. By pulling the drawstring 421 in a direction P (in this example away from the axis X1), the operator may cause a radial contraction (shrinking) of the cuff 420, thereby wrapping (or securing) the latter around the sewing ring SR. The coupling of the valve V to the conduit 40 may thus be completed. FIG. 6A depicts a schematic view, seen from the top of the holder device 2, which shows an exemplary configuration of the conduit 40 when the coupling with the valve V is completed, with the sewing ring SR substantially entirely wrapped within the cuff 420.

In various embodiments, the cuff 420 may be sized and dimensioned to radially cover only the sewing ring SR without interfering with the orifice defined in the valve V for the passage of blood.

Figure 7:
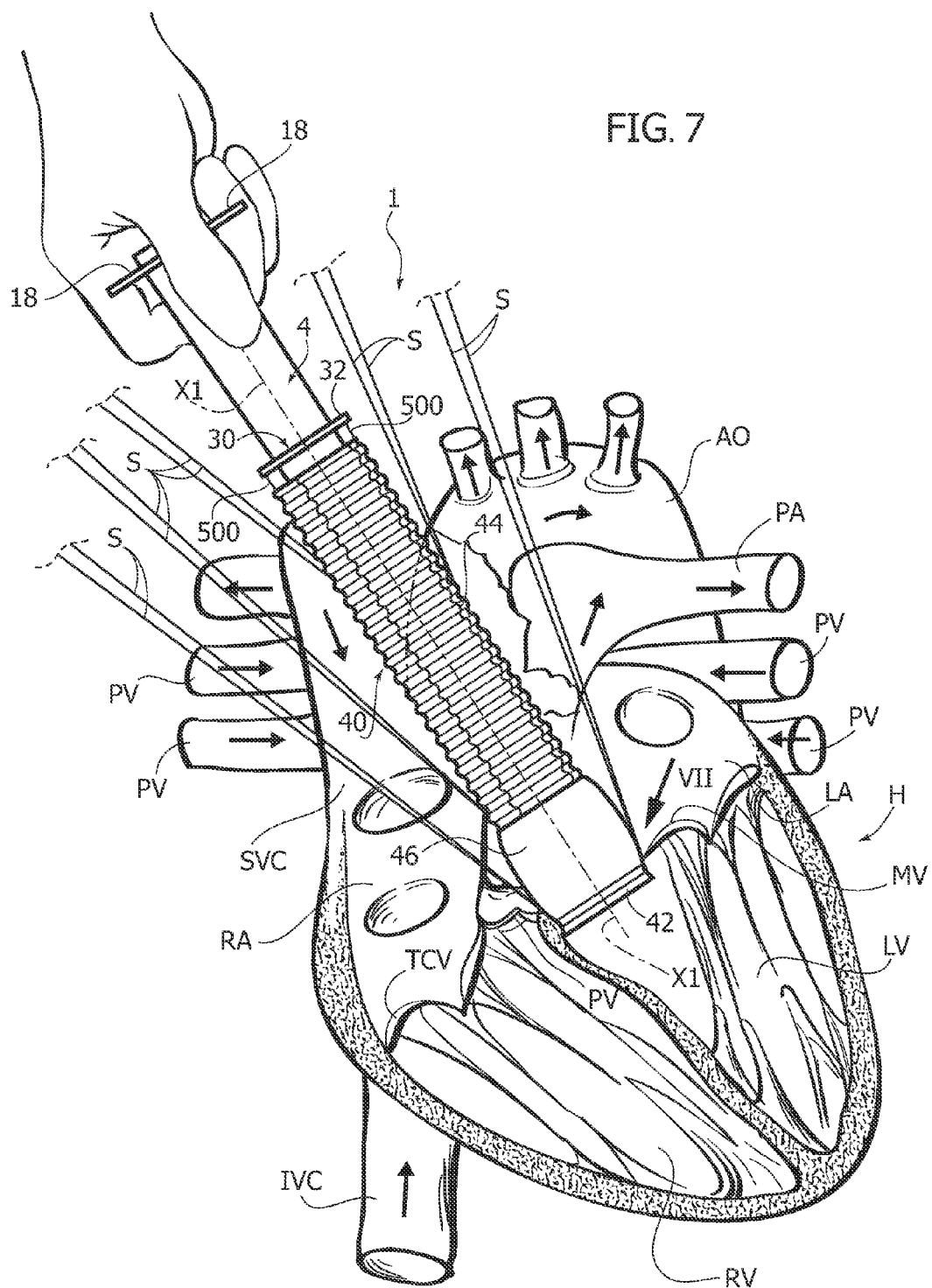

The implantation site may then be prepared for the implantation of the valved conduit. FIG. 7 shows a schematic view of a human heart H during the implantation of the valved conduit. The main blood vessels are labeled for prompt reference (the direction of blood flow is also shown). Such vessels include the aorta AO, the pulmonary veins PV, the pulmonary artery PA, the inferior vena cava IVC and the superior vena cava SVC. The natural heart valves schematically depicted in FIG. 7 include the pulmonary valve PV, the tricuspid valve TCV and the mitral valve MV. The aortic valve is not represented herein because in the example shown in FIG. 7 the valved conduit is intended for the implantation at the aortic annulus, wherein the valve V will replace the native aortic valve. The right atrium and the left atrium are indicated by RA and LA respectively, while the right ventricle and the left ventricle are indicated by RV and LV, respectively.

In various embodiments, suture threads S may be first passed through the aortic annulus at a number of positions therealong. The operator meanwhile may release the holder 2 from the base member 14 and pass it to the practitioner, who, in turn, may pass suture threads S through the cuff 42, the sewing ring SR and the cuff 42 again (see for reference FIG. 7A). The flared geometry of the sewing ring SR provided in various embodiments may offer an area to be pierced by suturing needles while passing the threads, while the hub 12 helps in preventing damages to the valve leaflets VL.

Figure 7A:
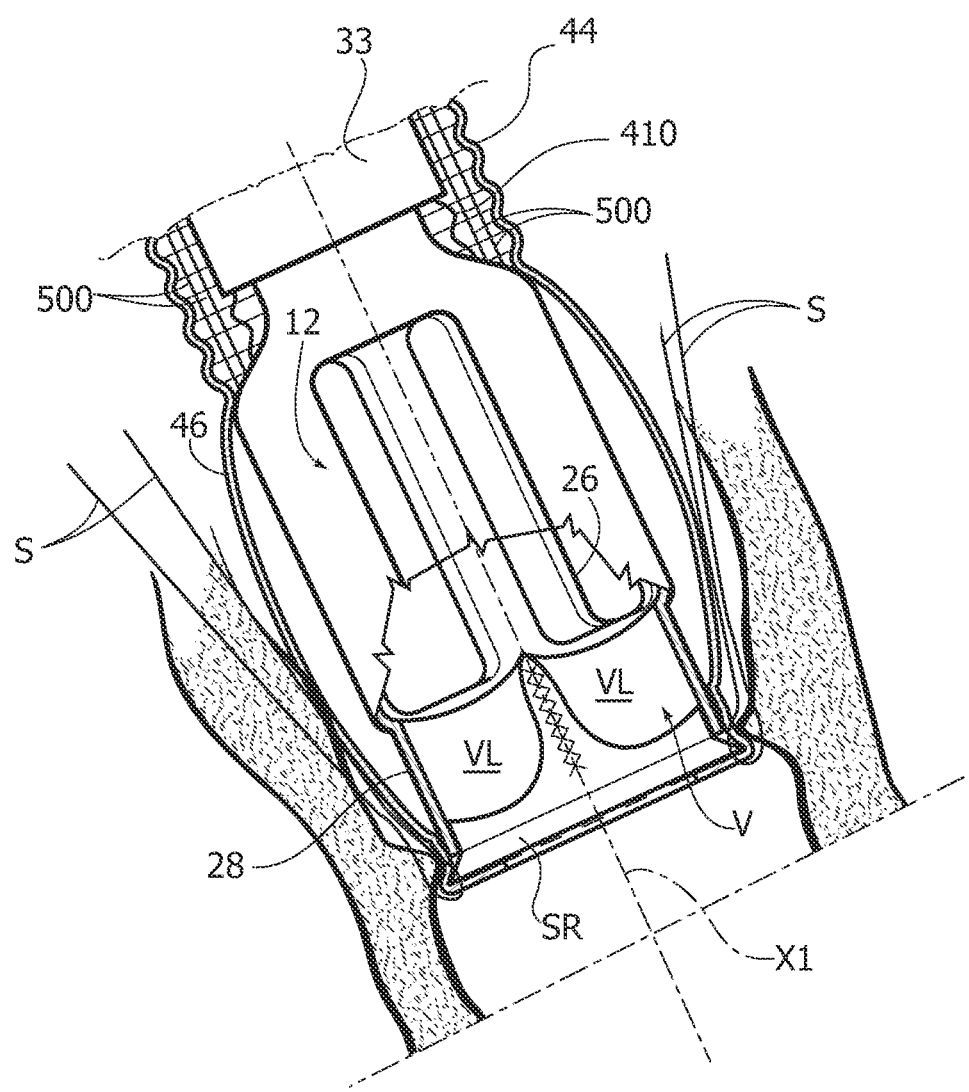

The practitioner may then "parachute" the valved conduit, still coupled to the holder device 2, along the threads S and reaches the implantation site (i.e. the aortic annulus). FIG. 7A shows how the stitching procedure creates a compressed pack of fabric layers aimed at achieving an effective fixation and minimizing leakage.

The valved conduit may then be secured to the implantation site by tying the suture threads S while it is still coupled to the holder device 2.

Figure 8:
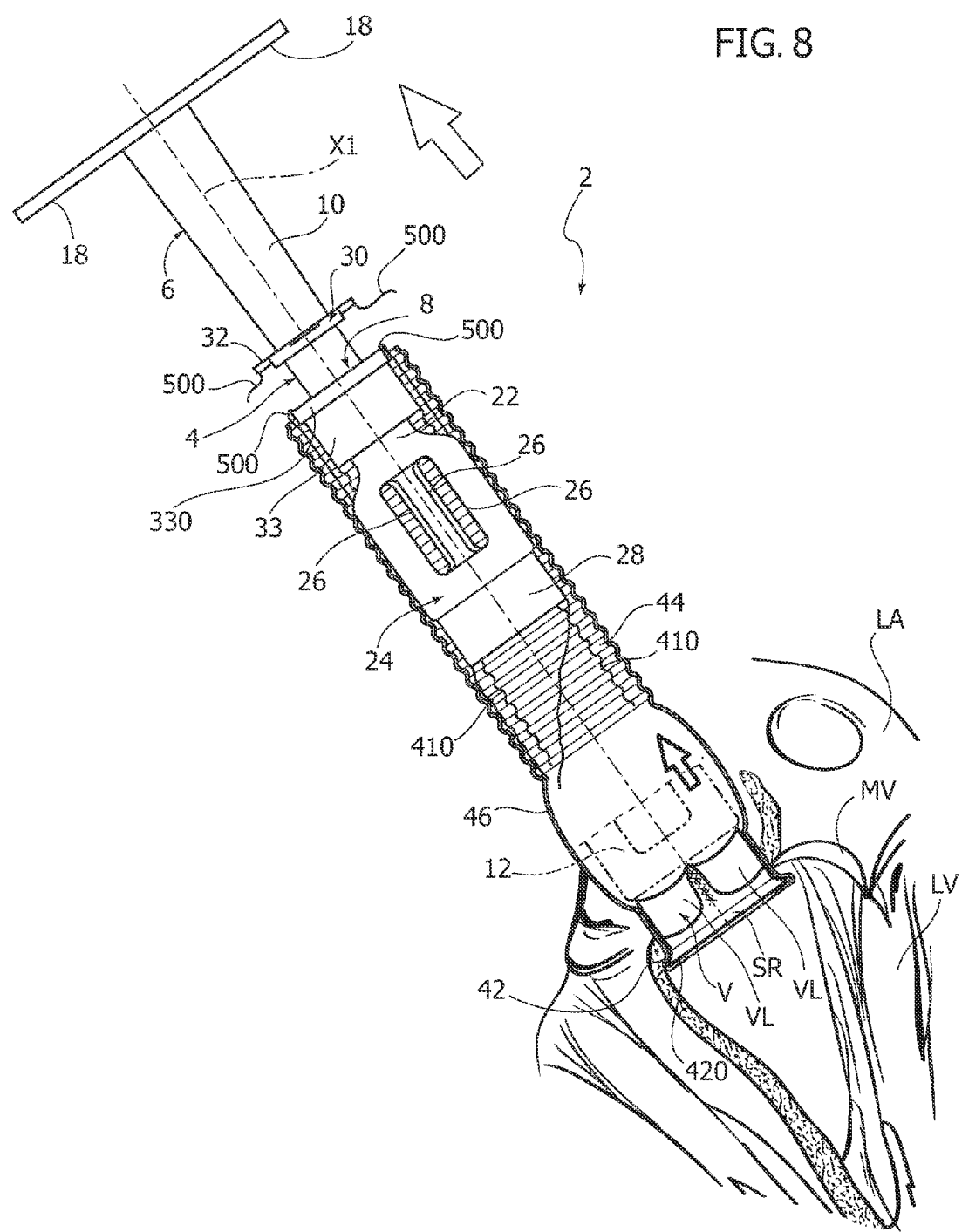

With reference to FIG. 8, the operator may complete the implantation of the valved conduit by cutting the threads 500 that secure the conduit 40 to the holder device 2. The holder device 2 may then be retracted (i.e., moved away) from the conduit 40 and the valve V, which remains firmly anchored to the implantation site.

For those embodiments where the threads 500 follow the path (or a similar configuration) shown in FIG. 3A, where the threads 500 extend between the flange 330 of the bushing 30 and the ring member 33, a portion of the threads 500 extending distally from the vascular conduit 40 are exposed. This exposed portion of the threads 500 may provide a convenient location at which the practitioner may cut the threads 500. Further, in such embodiments, as the threads 500 remain attached at one end to the bushing 30 and at another end to the ring member 33, upon removal of the holder device 2 from the conduit 40, all portions of the threads 500 will also be carried away from the implantation site.

Without prejudice to the underlying principles of the invention, the details and embodiments may vary, even significantly, with respect to what has been described herein, merely by way of example, without departing from the scope of the invention as defined by the annexed claims. Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The sewing ring SR of the valve V may have, in other embodiments, a shape which resembles that of a torus. In such embodiments, the outermost diameter (larger than an inner diameter of the receiving portion) of the torus shaped sewing ring may contact the inner side of the receiving portion 28 when the valve V is inserted within the hub 12 and the advancement of the valve V within the hub 12 may be stopped when such outermost diameter contacts and engages the receiving portion, for instance by interference therewith.

Additionally, preferred embodiments of the invention are included in the following examples.

Embodiment 1: a kit for the implantation of a prosthetic vascular conduit including:
  a prosthetic vascular conduit for coupling to a prosthetic valve having an annular portion, the prosthetic vascular conduit including a terminal collar member to receive the annular portion of the valve, wherein the terminal collar member includes a cuff which is radially contractible to engage the annular portion of the valve to couple the valve to the conduit,
  a holder device including a shaft and a hub located at an end of a proximal portion of the shaft, the hub including a receiving portion to house a prosthetic valve, wherein the prosthetic vascular conduit is fitted on the holder device so that at least a portion of the conduit adjacent to the cuff folds the receiving portion of the hub,
  a sleeve member fitted onto the conduit at a position corresponding to the receiving portion of the hub, wherein the cuff is wrapped on the sleeve member, and
  wherein the sleeve member is slidable away from the hub to unwrap the cuff the annular portion (SR) of a prosthetic valve housed within the receiving portion of the hub.

Embodiment 2: the kit of embodiment 1, wherein the cuff is located at an end portion of the collar member.

Embodiment 3: the kit of embodiment 1 or 2, wherein the cuff has a purse-string design including a drawstring passing through the cuff in and out along a marginal edge thereof.

Embodiment 4: the kit of any of the previous embodiments, wherein the terminal collar member of the conduit is anchored to the sleeve member by means of a first set of anchoring threads.

Embodiment 5: the kit of embodiment 4, wherein the first set of anchoring threads is passed through the cuff, wherein the sleeve member can be slid away from the conduit once the anchoring threads of the first set are defeated.

Embodiment 6: The kit of any of the previous claims, wherein the conduit is anchored to the holder device by means of a second set of anchoring threads.

Embodiment 7: the kit of embodiment 5, further including a ring member rigidly connected to the shaft, the anchoring threads of the second set being secured to the ring member.

Embodiment 8: the kit of any of the previous embodiments, wherein the shaft includes a handle provided at a distal portion thereof.

Embodiment 9: the kit of any of the previous embodiments, wherein at an end of the distal portion there are provided coupling means for coupling the holder device to a base member.

Embodiment 10. the kit (1) of any of the previous embodiments, wherein the cuff is formed of a material permitting suturing of the annular portion of a prosthetic heart valve to the conduit.

Embodiment 11: the kit of embodiment 10, wherein the annular portion is a sewing ring of the prosthetic heart valve.

Embodiment 12. the kit of any of the previous embodiments, wherein the cuff includes at least one angular marker for angularly referencing a prosthetic heart valve with respect to the cuff.

Embodiment 13: the kit of any of the previous embodiments, wherein the conduit includes a radially expandable portion adjacent the collar member.

Embodiment 14: a method of making a prosthetic valved conduit, the method including the steps of:
- providing a kit according to any of the previous embodiments;
- providing a prosthetic heart valve having an annular portion;
- advancing the heart valve prosthesis into the receiving portion of the hub until the annular portion of the prosthetic heart valve contacts the receiving portion;
- sliding the sleeve member away from the hub to unwrap the cuff of the prosthetic vascular conduit around the annular portion of the prosthetic heart valve, and
- wrapping the cuff of the prosthetic vascular conduit around the annular portion of the prosthetic heart valve by providing a radial contraction of the cuff.

Embodiment 15: the method of embodiment 14, wherein the cuff has a purse-string design including a drawstring passing through the cuff in and out along a marginal edge thereof, and wherein the step of wrapping the cuff is performed by pulling the drawstring.

The invention claimed is:

1. A kit for assembling a prosthetic vascular conduit, the kit comprising:
   a prosthetic vascular conduit configured to be coupled to a prosthetic valve having an annular portion, the prosthetic vascular conduit including a terminal collar member adapted to receive the annular portion of the valve, the terminal collar member including a portion that is radially contractible to engage the annular portion of the valve to couple the valve to the conduit;
   a holder device including a shaft and a hub located at an end of a proximal portion of the shaft, the hub including a receiving portion including an inner portion to house the prosthetic valve and an outer portion, wherein the prosthetic vascular conduit is fitted on the holder device so that at least a portion of the conduit adjacent to the terminal collar member surrounds the receiving portion of the hub and contacts the outer portion of the receiving portion; and
   a sleeve member fitted onto and surrounding the conduit at a position corresponding to the receiving portion of the hub, wherein an inner surface of the sleeve member contacts the conduit and the terminal collar member is wrapped at least partially over and around the sleeve member such that the terminal collar member contacts an outer surface of the sleeve member;
   wherein the sleeve member is removable from the hub so as to cause the terminal collar member to lose contact with the inner and outer surfaces of the sleeve member and be wrapped around the annular portion of the prosthetic valve when the prosthetic valve is housed within the inner portion of the receiving portion of the hub.

2. The kit of claim 1, wherein a cuff is located at or near an end portion of the terminal collar member.

3. The kit of claim 2, wherein the cuff has a purse-string design including a drawstring passing through the cuff in and out along a marginal edge thereof.

4. The kit of claim 2, wherein the terminal collar member of the conduit is anchored to the sleeve member via a first set of anchoring threads.

5. The kit of claim 4, wherein the first set of anchoring threads is passed through the cuff and wherein the sleeve member can be removed from the conduit once the anchoring threads of the first set are defeated.

6. The kit of claim 4, wherein the conduit is anchored to the holder device via a second set of anchoring threads.

7. The kit of claim 6, further including a ring member rigidly connected to the shaft, the anchoring threads of the second set being secured to the ring member.

8. The kit of claim 2, wherein the cuff is formed of a material permitting suturing of the annular portion of the prosthetic valve to the conduit.

9. The kit of claim 8, wherein the annular portion is a sewing ring of the prosthetic valve.

10. The kit of claim 1, wherein the shaft includes a handle provided at a distal portion thereof.

11. The kit of claim 10, further comprising a coupling mechanism for coupling the holder device to a base member, the coupling mechanism disposed at an end of the distal portion of the shaft.

12. The kit of claim 1, wherein the terminal collar member includes at least one angular marker for angularly referencing the prosthetic valve with respect to the terminal collar member.

13. The kit of claim 1, wherein the conduit includes a radially expandable portion adjacent the terminal collar member.

14. A kit for assembling a prosthetic vascular conduit, the kit comprising:
   a prosthetic vascular conduit configured to be coupled to a prosthetic valve having an annular portion, the prosthetic vascular conduit including a terminal collar member adapted to receive the annular portion of the valve, the terminal collar member including a portion that is radially contractible to engage the annular portion of the valve to couple the valve to the conduit;
   a holder device including a shaft and a hub located at an end of a proximal portion of the shaft, the hub including a receiving portion including an inner portion to house the prosthetic valve and an outer portion, wherein the prosthetic vascular conduit is fitted on the holder device so that at least a portion of the conduit adjacent to the terminal collar member surrounds the receiving portion of the hub and contacts the outer portion of the receiving portion; and
   a sleeve member fitted onto and surrounding the conduit at a position corresponding to the receiving portion of the hub, wherein an inner surface of the sleeve member contacts the conduit and the terminal collar member is wrapped at least partially over and around the sleeve member such that the terminal collar member contacts an outer surface of the sleeve member, and wherein an inner diameter of the sleeve member is sized and dimensioned to accommodate the conduit and the terminal collar member;
   wherein the sleeve member is removable from the hub so as to cause the terminal collar member to lose contact with the inner and outer surfaces of the sleeve member and be wrapped around the annular portion of the prosthetic valve once the prosthetic valve is housed within the inner portion of the receiving portion of the hub.

15. The kit of claim 14, wherein the inner diameter of the sleeve member exceeds an outer diameter of the terminal collar member by substantially twice a wall thickness of the conduit.

16. A kit for assembling a prosthetic vascular conduit, the kit comprising:

a prosthetic vascular conduit configured to be coupled to a prosthetic valve having an annular portion, the prosthetic vascular conduit including a terminal collar member adapted to receive the annular portion of the valve, the terminal collar member including a portion that is radially contractible to engage the annular portion of the valve to couple the valve to the conduit;

a holder assembly including a shaft comprising a distal portion and a proximal portion, and a hub located at an end of the proximal portion of the shaft, wherein the distal portion and proximal portions are separate and may be removably coupled, the distal portion includes a handle, the distal portion includes a coupling mechanism for being removably coupled to a base member in order to render the holder assembly self-standing, the hub including a receiving portion including an inner portion to house the prosthetic valve and an outer portion, wherein the prosthetic vascular conduit is fitted on the holder assembly so that at least a portion of the conduit adjacent to the terminal collar member surrounds the receiving portion of the hub and contacts the outer portion of the receiving portion; and a sleeve member fitted onto and surrounding the conduit at a position corresponding to the receiving portion of the hub, wherein an inner surface of the sleeve member contacts the conduit and the terminal collar member is wrapped at least partially over and around the sleeve member such that the terminal collar member contacts an outer surface of the sleeve member;

wherein the sleeve member is removable from the hub so as to cause the terminal collar member to lose contact with the inner and outer surfaces of the sleeve member and be wrapped around the annular portion of the prosthetic valve when the prosthetic valve is housed within the inner portion of the receiving portion of the hub.

17. The kit of claim 16, wherein the receiving portion of the hub includes at least one window.

* * * * *